(12) United States Patent  (10) Patent No.: US 8,344,365 B2
Kim et al.  (45) Date of Patent: Jan. 1, 2013

(54) ORGANIC LIGHT EMITTING DEVICE

(75) Inventors: Young-Kook Kim, Yongin (KR);
Seok-Hwan Hwang, Yongin (KR);
Yoon-Hyun Kwak, Yongin (KR);
Hye-Jin Jung, Yongin (KR); Jong-Hyuk Lee, Yongin (KR); Jin-O Lim, Yongin (KR); Hee-Joo Ko, Yongin (KR)

(73) Assignee: Samsung Display Co., Ltd., Yongin (KR)

( * ) Notice: Subject to any disclaimer, the term of this patent is extended or adjusted under 35 U.S.C. 154(b) by 61 days.

(21) Appl. No.: 12/854,056

(22) Filed: Aug. 10, 2010

(65) Prior Publication Data

US 2011/0037060 A1 Feb. 17, 2011

(30) Foreign Application Priority Data

Aug. 14, 2009 (KR) .................. 10-2009-0075330

(51) Int. Cl.
*H01L 51/00* (2006.01)
(52) U.S. Cl. .................. 257/40; 257/E51.001
(58) Field of Classification Search .............. 257/40
See application file for complete search history.

(56) References Cited

U.S. PATENT DOCUMENTS

| 5,645,948 | A | 7/1997 | Shi et al. |
| 6,529,541 | B1 | 3/2003 | Ueki et al. |
| 6,650,683 | B2 | 11/2003 | Ueki et al. |
| 2005/0176953 | A1 | 8/2005 | Tuan et al. |
| 2009/0058289 | A1* | 3/2009 | Stoessel et al. ............... 313/504 |

FOREIGN PATENT DOCUMENTS

| JP | 2005093159 | 4/2005 |
| JP | 2008028424 | 2/2008 |
| KR | 1020050089717 A | 9/2005 |
| KR | 1020080108329 A | 12/2008 |

OTHER PUBLICATIONS

New Napthoindole containing AZO dyes, by E.N. Elizbarashvili et al., No. 4 2006, ISSN 0005-2531, p. 71-75.*
European Search Report dated Dec. 29, 2010, for corresponding European Patent application 10251442.9, noting listed Category X references in this IDS.
Buu-Hoï, N.P., et al, No. 105—*Une modification àla methode de Huang-Minion pour la réduction des acides β-aroylpropioniques; quelques applicaitons*, Mémoires Présentés A La Société Chimique, May 1, 1966, pp. 624-627, XP 009140718.
Buu-Hoï, N.P., et al, *Carcinogenic Nitrogen Compounds. Part XLI. Pyridocarbazoles and Analogous Heterocycles Derived from Isoquinolyulhydroazines*, Journal of the Chemical Society, vol. 1964, Sep. 1, 1954, pp. 3924-3927, XP 009140714.
Buu-Hoï, N.P., et al, *Carcinogenic Nitrogen Compounds. Part XLIV. Naphtho- and Phenanthrocarbazoles*, Journal of the Chemical Society, Jan. 1, 1965, pp. 2642-2645, XP 009140717.

(Continued)

*Primary Examiner* — Wai Sing Louie
(74) *Attorney, Agent, or Firm* — Christie, Parker & Hale, LLP

(57) ABSTRACT

Embodiments of the present invention are directed to a heterocyclic compound and an organic light-emitting device including the heterocyclic compound. The organic light-emitting devices using the heterocyclic compounds have high-efficiency, low driving voltage, high luminance and long lifespan.

17 Claims, 1 Drawing Sheet

OTHER PUBLICATIONS

Buu-Hoï, N.P., et al, *Carcinogenic Nitrogen Compounds. Part XXXII. The Synthesis of New Highly Active Benzopyridocarbazoles*, Journal of the Chemical Society, Jan. 1, 1962, pp. 146-150, XP 009140858.

Ph, Ng, et al, *Carcinogenic Nitrogen Compounds. Part XXVIII. Azadibenzofluorenes and Related Compounds*, Journal of the Chemical Society, Jan. 1, 1960, pp. 4500-4503, XP 009140854.

Ph, Ng, et al, *Carcinogenic Nitrogen Compounds. Part XVIII. The Synthesis of Some Polycyclic Carbazoles*, Journal of the Chemical Society, Jan. 1, 1956, pp. 1515-1518, XP 009140860.

Lauer, J.C., et al, *Improved characterization of coal tar distillation cuts (200-500° C)*, Fuel, vol. 67, Oct. 1, 1988, pp. 1446-1455, XP 002608733.

Buu-Hoï, N.P., et al, *The Effect of Benzocarbazoles and Benzacridines on the Paralysing Action of Zoxazolamine; Structure/Activity Relationships*, Biochemical Pharmacology, vol. 17, Jan. 1, 1968, pp. 1227-1236, XP 002608734.

Sawicki, E., et al., *Chromatographic Separation and Spectral Analysis of Polynuclear Aromatic Amines and Heterocyclic Imines*, Microchemical Journal, vol. 10, Jan. 1, 1966, pp. 72-102, XP 002608735.

Lacassagne, A., et al., *Cancérologie.—Activitésarcomogène chez deux nouveaux types d'hétérocycles: les benzocarbolines et les thiénopyridocarbazoles*, Comptes Rendues de L'Academie Scientifique de Paris, vol. 271, Oct. 19, 1970, pp. 1474-1479, XP 009140701.

KIPO Office action dated Apr. 21, 2011, for Korean priority Patent application 10-2009-0075330, noting listed references in this IDS, as well as other references previously submitted in an IDS dated Mar. 21, 2011, 7 pages.

Bigot, P., et al., *Carcinogenic nitrogen compounds. LXXXII. Polycyclic indoles by the Mohlau-Bischler synthesis*, Journal of the Chemical Society, (1972), vol. 20, pp. 2573-2576, Accession No. 77:151801, 1 page.

Epstein, S., et al., *Association between photodynamic and enzyme-inducing activities in polycyclic compounds*, Cancer Research, vol. 31, No. 8 (1971), pp. 1087-1094, Accession No. 75:96680, 1 page.

Elizbarashvili, E., et al., *New naphthoindole containing azo dyes*, Azerbaidzhanskii Khimicheskii Zhurnal, vol. 4 (2006), pp. 71-75, Accession No. 150:6943, 1 page.

Wise, S.A., et al., *Characterization of polycyclic aromatic hydrocarbon minerals, curtisite, idrialite and pendletonite using high performance liquid chromatography, gas chromatography, mass spectrometry and nuclear magnetic resonance spectroscopy*, Chemical Geology, vol. 54, No. 3-4, (1986), pp. 339-357, Accession No. 104:210122, 1 page.

KIPO Registration Determination Certificate dated Aug. 31, 2012, for Korean priority Patent application 10-2009-0075330, (5 pages).

* cited by examiner

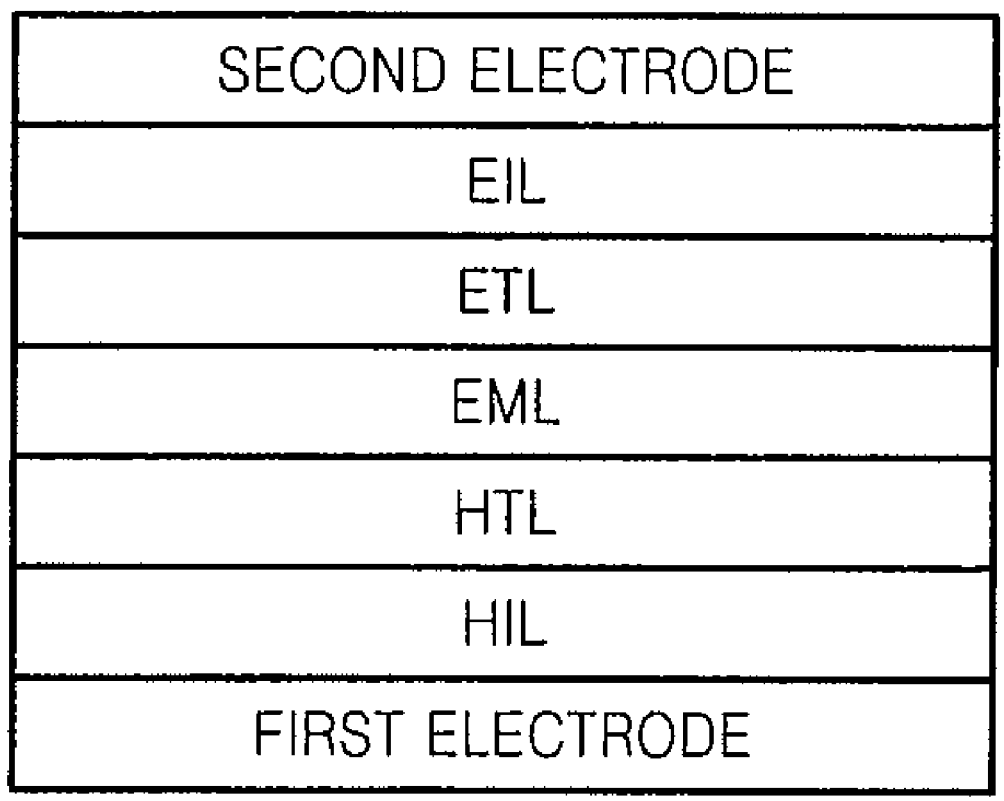

ORGANIC LIGHT EMITTING DEVICE

CROSS-REFERENCE TO RELATED PATENT APPLICATION

This application claims priority to and the benefit of Korean Patent Application No. 10-2009-0075330, filed on Aug. 14, 2009, in the Korean Intellectual Property Office, the entire content of which is incorporated herein by reference.

BACKGROUND OF THE INVENTION

1. Field of the Invention

The present invention relates to heterocyclic compounds and organic light-emitting devices including the heterocyclic compounds.

2. Description of the Related Art

Organic light-emitting devices are self-emission type display devices and have wide viewing angles, high contrast ratios, and short response times. Due to these characteristics, organic light-emitting devices are drawing more attention.

Such organic light-emitting devices can be roughly classified into inorganic light-emitting devices which include emission layers containing inorganic compounds, and organic light-emitting devices which include emission layers containing organic compounds. Organic light-emitting devices have higher luminance, lower driving voltages, and shorter response times than inorganic light-emitting devices, and can render multi-colored displays. In addition, organic light-emitting devices produce various colors. Thus, much research into such organic light-emitting devices has been conducted.

Typically, an organic light-emitting device has a stack structure including an anode, a cathode and an organic emission layer between the anode and cathode. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode structure or an anode/hole transport layer/organic emission layer/electron transport layer/cathode structure.

As the material for forming the hole transport layer, polyphenyl compounds or anthracene derivatives can be used. However, organic light-emitting devices including hole injection layers and/or hole transport layers formed of such materials do not have satisfactory life span, efficiency, and power consumption characteristics, thus leaving much room for improvement.

SUMMARY OF THE INVENTION

According to embodiments of the present invention, a heterocyclic compound imparts improved electrical characteristics, charge transporting capabilities and light-emission capabilities.

In some embodiments of the present invention, an organic light-emitting device includes the heterocyclic compound.

According to other embodiments of the present invention, a flat panel display device includes the organic light-emitting device.

In still other embodiments of the present invention, an organic light-emitting device comprises at least one layer containing the heterocyclic compound, where the at least one layer is formed using a wet process.

According to embodiments of the present invention, a heterocyclic compound is represented by Formula 1 below:

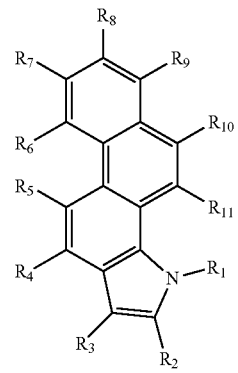

Formula 1

In Formula 1, each of $R_1$ through $R_{11}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with a $C_5$-$C_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Two or more adjacent groups selected from $R_1$ through $R_{11}$ may optionally join to form an aromatic ring.

$R_9$ may be selected from unsubstituted monocyclic to tetracyclic aryl groups, unsubstituted $C_4$-$C_{60}$ heteroaryl groups, unsubstituted $C_5$-$C_{50}$ arylamine groups, substituted monocyclic to tetracyclic aryl groups, substituted $C_4$-$C_{60}$ heteroaryl groups, and substituted $C_5$-$C_{50}$ arylamine groups Nonlimiting examples of suitable unsubstituted monocyclic to tetracyclic aryl groups include phenyl groups, naphthyl groups, biphenyl groups, terphenyl groups, anthracenyl groups, fluorenyl groups, carbazolyl groups, and pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups substituted with at least one substituent selected from $C_1$-$C_5$ alkyl groups, $C_1$-$C_5$ alkoxy groups, cyano groups, amine groups, phenoxy groups, phenyl groups and halogen groups. Nonlimiting examples of suitable substituted $C_4$-$C_{60}$ heteroaryl groups include those that are substituted with at least one substituent selected from $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups. Nonlimiting examples of suitable substituted $C_5$-$C_{50}$ arylamine groups include those that are substituted with at least one substituent selected from $C_1$-$C_5$ alkyl groups, $C_1$-$C_5$ alkoxy groups, cyano groups, amine groups, phenoxy groups, phenyl groups and halogen groups.

$R_1$ may be selected from unsubstituted monocyclic to tetracyclic aryl groups, an unsubstituted $C_4$-$C_{60}$ heteroaryl groups, substituted monocyclic to tetracyclic aryl groups, and substituted $C_4$-$C_{60}$ heteroaryl groups. Nonlimiting examples of suitable unsubstituted monocyclic to tetracyclic aryl groups include phenyl groups, naphthyl groups, biphenyl groups, terphenyl groups, anthracenyl groups, fluorenyl groups, carbazolyl groups, and pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups substituted with at least one substituent selected from $C_1$-$C_5$ alkyl groups, $C_1$-$C_5$ alkoxy groups, cyano groups, amine groups, phenoxy groups, phenyl groups, and halogen groups. Nonlimiting examples of suitable substituted $C_4$-$C_{60}$ heteroaryl groups include those that are substituted with at least one substituent selected from $C_1$-$C_5$ alkyl groups, $C_1$-$C_5$ alkoxy groups, cyano groups, amine groups, phenoxy groups, phenyl groups, and halogen groups.

Each of $R_2$ and $R_3$ may be independently selected from methyl groups and phenyl groups.

The heterocyclic compound may include one of Compounds 3, 13, 19 and 29 below:

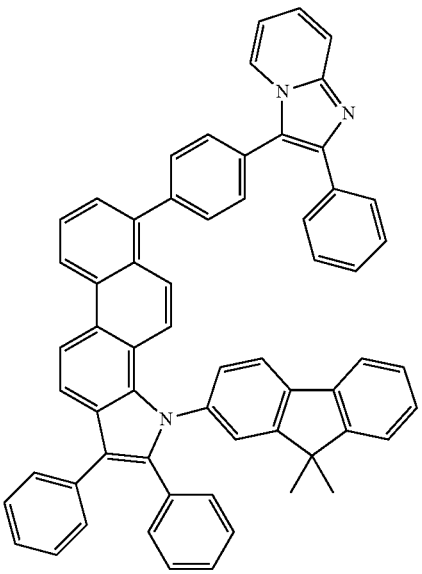

According to embodiments of the present invention, an organic light-emitting device includes a first electrode, a second electrode, and an organic layer between the first electrode and the second electrode, wherein the organic layer includes the heterocyclic compound described above.

According to other embodiments of the present invention, the organic layer may include an electron injection layer or an electron transport layer.

According to still other embodiments of the present invention, the organic layer may include a single layer having both electron injection and electron transport capabilities.

According to yet other embodiments of the present invention, the organic layer may include an emission layer.

According to embodiments of the present invention, the organic layer may include an emission layer, and the heterocyclic compound may be a fluorescent or phosphorescent host.

According to embodiments of the present invention, the organic layer may include an emission layer, and the heterocyclic compound may be a fluorescent dopant.

According to embodiments of the present invention, the organic layer may include an emission layer, and an electron injection layer or an electron transport layer, wherein the emission layer includes an anthracene compound.

According to embodiments of the present invention, the organic layer may include an emission layer, and an electron injection layer or an electron transport layer, wherein the emission layer includes an arylamine compound.

According to embodiments of the present invention, the organic layer may include an emission layer, and an electron injection layer or an electron transport layer, wherein the emission layer includes a styryl compound.

According to embodiments of the present invention, the organic layer may include an emission layer, and an electron injection layer or an electron transport layer, and the emission layer may include a red emission layer, a green emission layer, a blue emission layer or a white emission layer that includes a phosphorescent compound.

According to embodiments of the present invention, the organic layer may include at least one layer selected from a hole injection layer, a hole transport layer, an electron blocking layer, an emission layer, a hole blocking layer, an electron transport layer, and an electron injection layer.

According to embodiments of the present invention, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

According to other embodiments of the present invention, a flat panel display device includes the organic light-emitting device described above, wherein the first electrode of the organic light-emitting device is electrically connected to a source electrode or a drain electrode of a thin-film transistor.

According to other embodiments of the present invention, an organic light-emitting device includes a first electrode, a second electrode, and an organic layer between the first electrode and the second electrode, wherein the organic layer includes at least one layer including the heterocyclic compound of claim 1, the at least one layer being formed using a wet process.

BRIEF DESCRIPTION OF THE DRAWING

The above and other features and advantages of the present invention will become more apparent by reference to the following detailed description when considered in conjunction with the attached drawing in which:

FIG. 1 is a diagram of the structure of an organic light-emitting device according to an embodiment of the present invention.

DETAILED DESCRIPTION OF THE INVENTION

The present invention will now be described with reference to the accompanying drawings, in which exemplary embodiments of the invention are shown.

A heterocyclic compound according to embodiments of the present invention is represented by Formula 1 below:

Formula 1

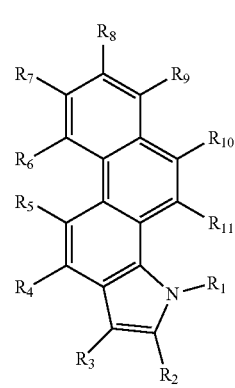

In Formula 1, each of $R_1$ through $R_{11}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $C_5$-$C_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Two or more adjacent groups selected from $R_1$ through $R_{11}$ may combine to form an aromatic ring.

Nonlimiting examples of suitable materials for forming an emission layer or electron transport layer of an organic light-emitting device include Alq$_3$, 2,2',2"-(1,3,5-phenylene)tris-(1-phenyl)-1H-benzimidazole (TPBI), 2-biphenyl-4-yl-5-(4-tert-butyl-phenyl)-[1,3,4]oxadiazole (PBD), PF-6P (perfluoronated chemical), and 2,5-bis(6'-(2',2"-bipyridyl))-1,1-dimethyl-3,4-diphenylsilylol (PyPySPyPy). However, organic light-emitting devices manufactured using these materials do not have satisfactory lifespan, efficiency, and power consumption characteristics, leaving much room for improvement.

Organic light-emitting devices manufactured using heterocyclic compounds of Formula 1 (in which a phenanthrene group and an indole group are fused to each other) have good durability when stored or operated. In addition, due to the introduction of a substituent such as a fluorene group or a naphthyl group, molecular layers formed as thin films may be maintained in good condition, thereby improving the characteristics of the organic light-emitting device.

Substituents in the heterocyclic compound of Formula 1 will now be described. $R_9$ may be selected from unsubstituted monocyclic to tetracyclic aryl groups, unsubstituted $C_4$-$C_{60}$ heteroaryl groups, unsubstituted $C_5$-$C_{50}$ arylamine groups, substituted monocyclic to tetracyclic aryl groups, substituted $C_4$-$C_{60}$ heteroaryl groups, and substituted $C_5$-$C_{50}$ arylamine groups. Nonlimiting examples of suitable unsubstituted monocyclic to tetracyclic aryl groups include phenyl groups, naphthyl groups, biphenyl groups, terphenyl groups, anthracenyl groups, fluorenyl groups, carbazolyl groups, and pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups substituted with at least one substituent selected from $C_1$-$C_5$ alkyl groups, $C_1$-$C_5$ alkoxy groups, cyano groups, amine groups, phenoxy groups, phenyl groups, and halogen groups. Nonlimiting examples of suitable substituted $C_4$-$C_{60}$ heteroaryl groups include those substituted with at least one substituent selected from $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups. Nonlimiting examples of suitable substituted $C_5$-$C_{50}$ arylamine groups include those substituted with at least one substituent selected from $C_1$-$C_5$ alkyl groups, $C_1$-$C_5$ alkoxy groups, cyano groups, amine groups, phenoxy groups, phenyl groups, and halogen groups.

$R_1$ may be selected from unsubstituted monocyclic to tetracyclic aryl groups, unsubstituted $C_4$-$C_{60}$ heteroaryl groups, substituted monocyclic to tetracyclic aryl groups, and substituted $C_4$-$C_{60}$ heteroaryl groups. Nonlimiting examples of suitable unsubstituted monocyclic to tetracyclic aryl groups include phenyl groups, naphthyl groups, biphenyl groups, terphenyl groups, anthracenyl groups, fluorenyl groups, carbazolyl groups, and pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups substituted with at least one substituent selected from $C_1$-$C_5$ alkyl groups, $C_1$-$C_5$ alkoxy groups, cyano groups, amine groups, phenoxy groups, phenyl groups, and halogen groups. Nonlimiting examples of suitable substituted $C_4$-$C_{60}$ heteroaryl groups include those substituted with at least one substituent selected from $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups.

Each of $R_2$ and $R_3$ may be independently selected from methyl groups and phenyl groups.

Substituents described with reference to Formula 1 will now be described. The unsubstituted $C_1$-$C_{50}$ alkyl group used herein may be linear or branched. Nonlimiting examples of the alkyl group include methyl groups, ethyl groups, propyl groups, isobutyl groups, sec-butyl groups, pentyl groups, isoamyl groups, hexyl groups, heptyl groups, octyl groups, nonanyl groups, and dodecyl groups. At least one hydrogen atom of the alkyl group may be substituted with a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_3$-$C_{50}$ cycloalkyl group indicates a cyclic alkyl group having 3 to 50 carbon atoms. One or more hydrogen atom of the $C_3$-$C_{50}$ cycloalkyl group may be substituted with a substituent such as those described with reference to the $C_1$-$C_{50}$ alkyl group.

The unsubstituted $C_1$-$C_{50}$ alkoxy group used herein is a group having a -OA structure where A is an unsubstituted $C_1$-$C_{50}$ alkyl group as described above. Nonlimiting examples of the alkoxy group include methoxy groups, ethoxy groups, propoxy groups, isopropyloxy groups, butoxy groups, and pentoxy groups. One or more hydrogen atom of the $C_1$-$C_{50}$ alkoxy group may be substituted with a substituent such as those described above with reference to the $C_1$-$C_{50}$ alkyl group.

The unsubstituted $C_5$-$C_{60}$ aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. In the aryl group, one or more hydrogen atoms may be substituted with a substituent such as those described above with reference to the $C_1$-$C_{50}$ alkyl group.

Nonlimiting examples of the substituted or unsubstituted $C_5$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-tolyl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyano naphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group used herein includes one, two or three hetero atoms selected from N, O, P and S. At least two rings may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In the hetero aryl group, one or more hydrogen atoms may be substituted with a substituent such as those described above with respect to the $C_1$-$C_{50}$ alkyl group.

The unsubstituted $C_5$-$C_{50}$ aryloxy group used herein is a group having a -$OA_1$ structure where $A_1$ is a functional group such as those described above with respect to the $C_5$-$C_{60}$ aryl group, but having a different number of carbon atoms. Nonlimiting examples of the unsubstituted $C_5$-$C_{50}$ aryloxy group include phenoxy groups. One or more hydrogen atoms of the unsubstituted $C_5$-$C_{50}$ aryloxy group may be substituted with a substituent such as those described above with respect to the unsubstituted $C_1$-$C_{50}$ alkyl group.

The unsubstituted $C_5$-$C_{50}$ arylthio group used herein is a group having a -$SA_1$ structure where $A_1$ is a functional group such as those described above with respect to the $C_5$-$C_{60}$ aryl group, but having a different number of carbon atoms. Nonlimiting examples of the unsubstituted $C_5$-$C_{50}$ arylthio group include phenylthio groups and naphthylthio groups. One or more hydrogen atoms of the $C_5$-$C_{50}$ arylthio group may be substituted with a substituent such as those described above with respect to the $C_1$-$C_{50}$ alkyl group.

The unsubstituted $C_6$-$C_{60}$ condensed polycyclic group used herein refers to a substituent including at least two rings in which at least one aromatic ring and/or at least one non-aromatic ring are fused to each other. The unsubstituted $C_6$-$C_{60}$ condensed polycyclic group may include at least one substituent such as those described with respect to the aryl group or the heteroaryl group.

The unsubstituted $C_5$-$C_{50}$ arylamine group refers to an amino group substituted with at least one $C_5$-$C_{50}$ aryl group.

Nonlimiting examples of the heterocyclic compound of Formula 1 include Compounds 1 through 36 represented below.
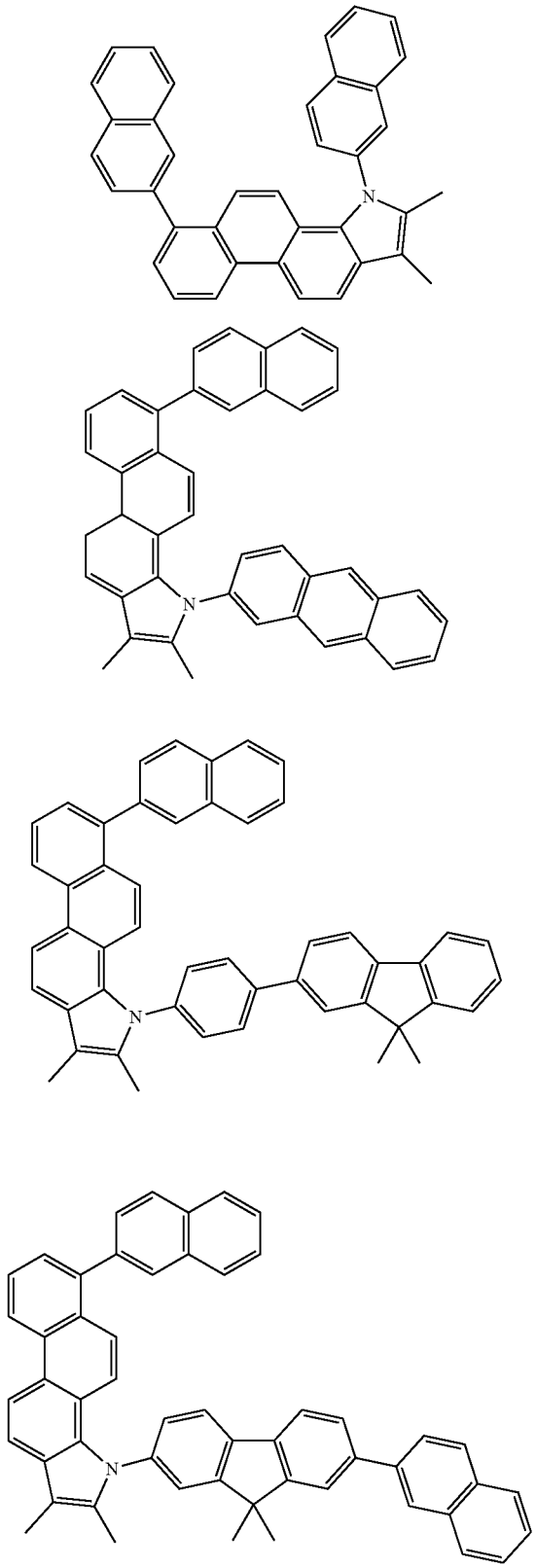
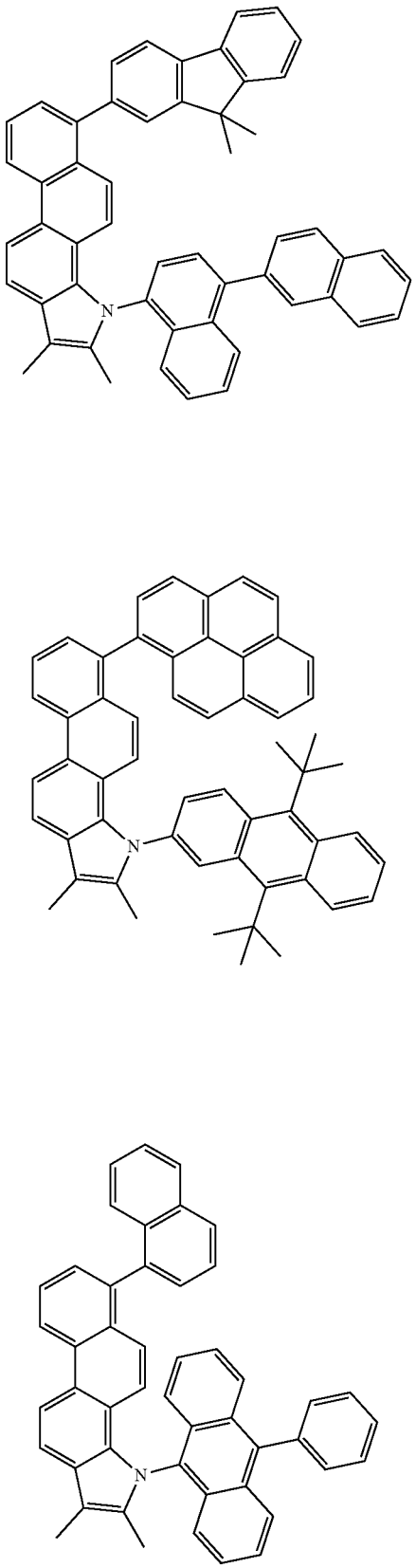

8
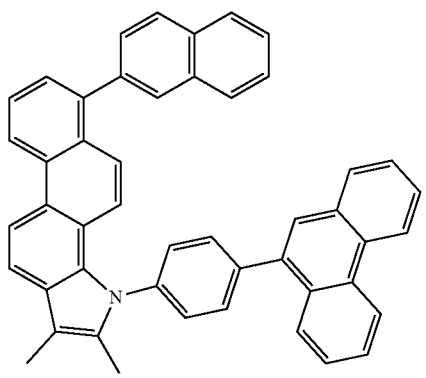
11
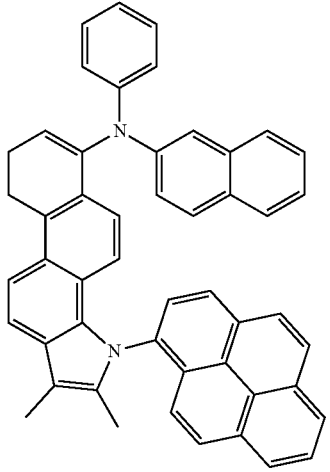
9
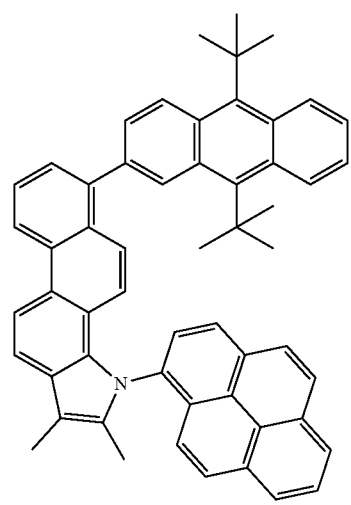
12
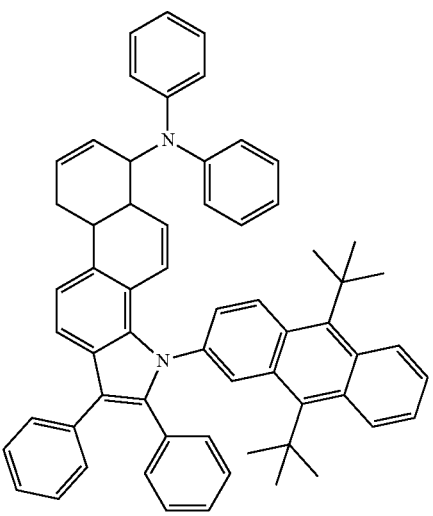
10
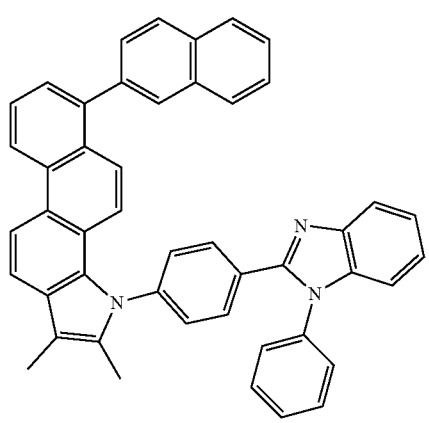
13
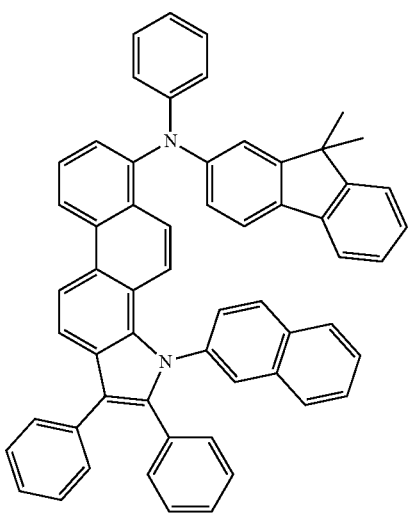

14
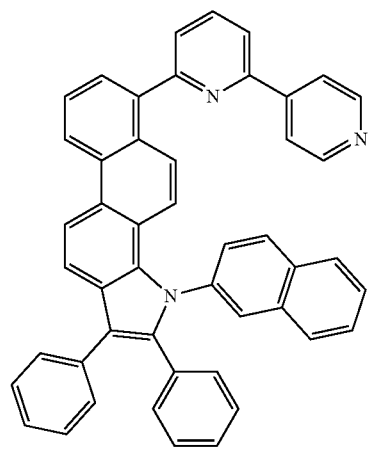
15
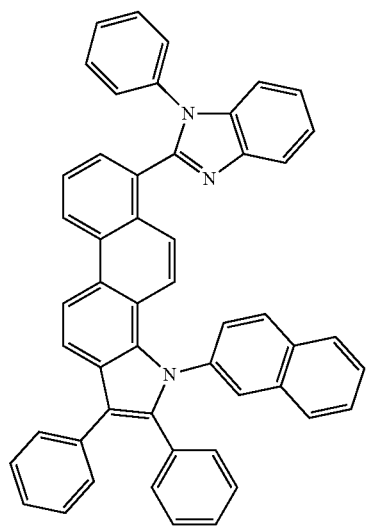
16
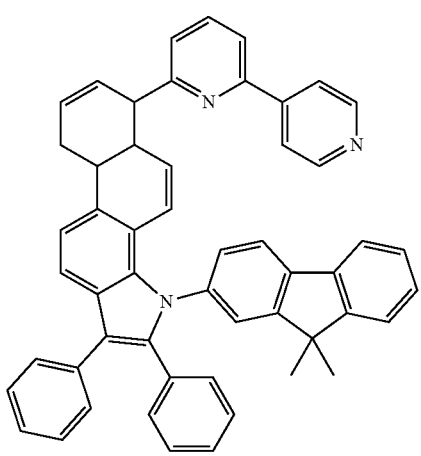
17
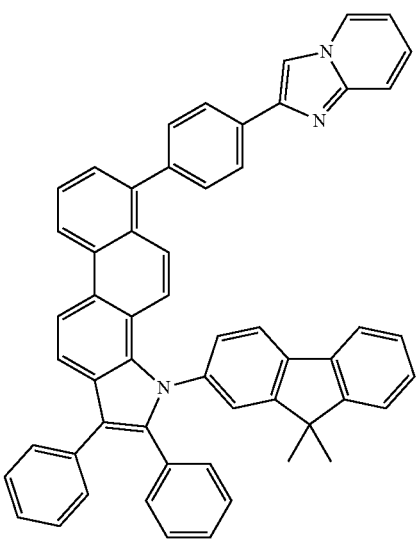
18
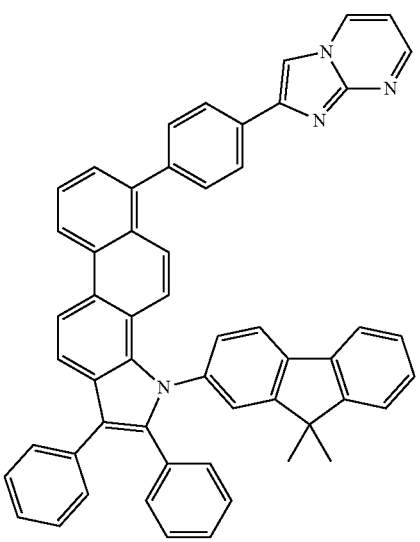
19
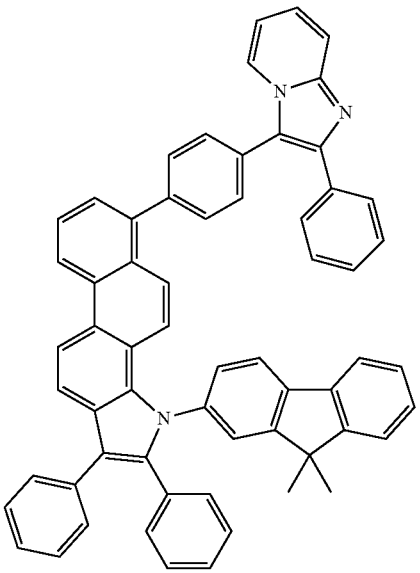

20
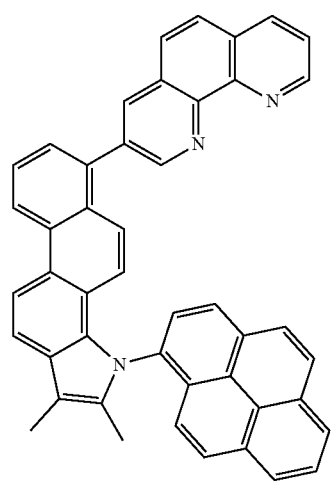
21
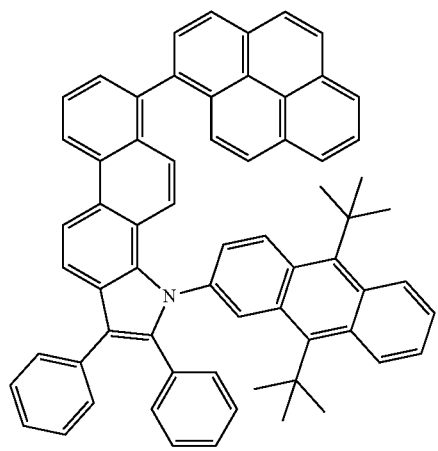
22
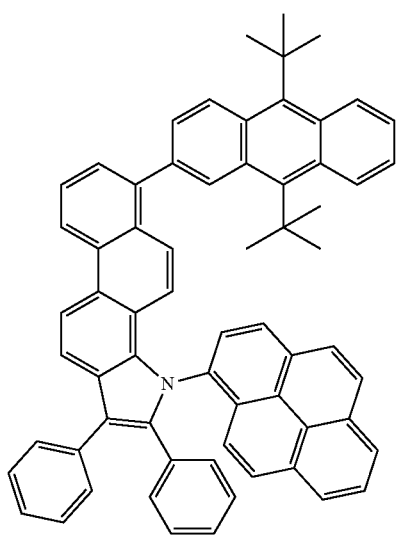
23
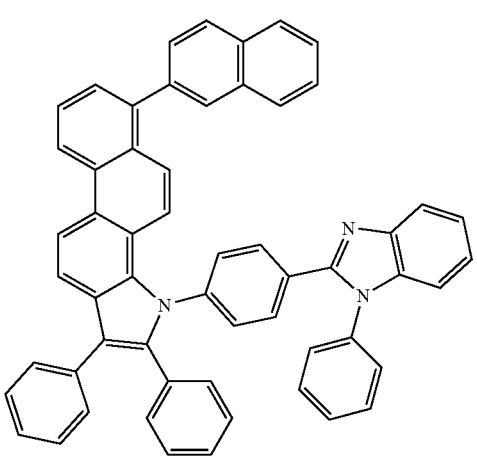
24
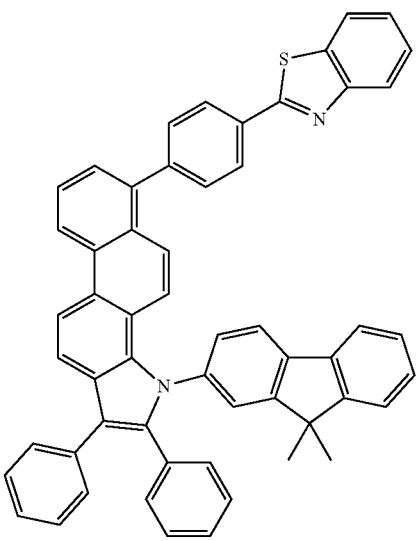
25
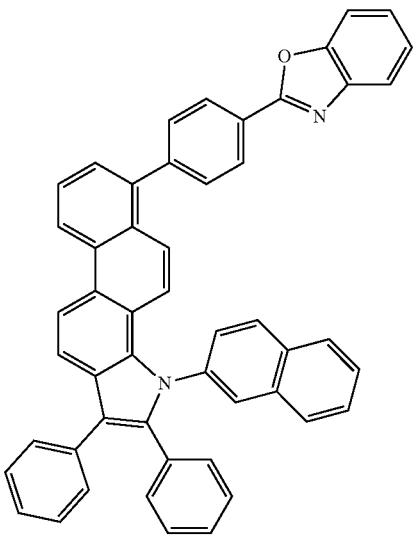

26
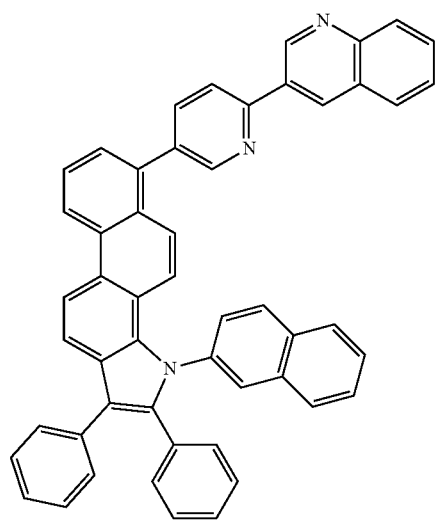
27
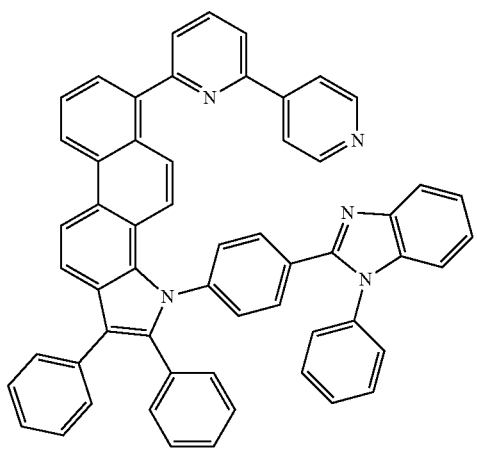
28
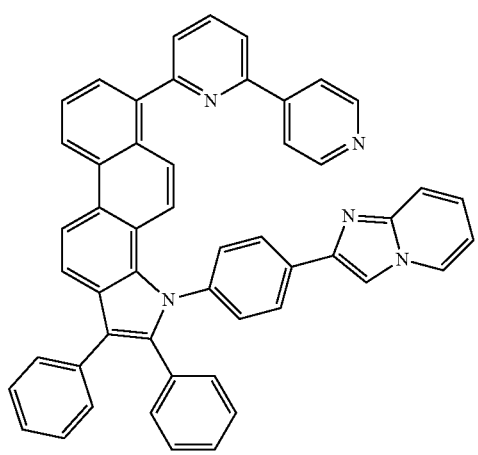
29
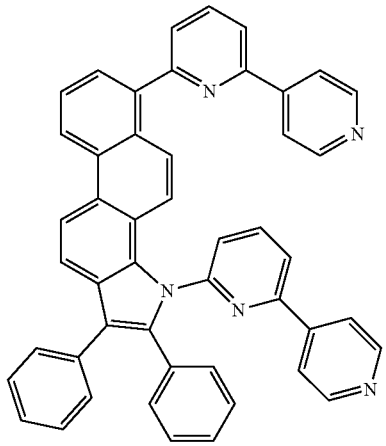
30
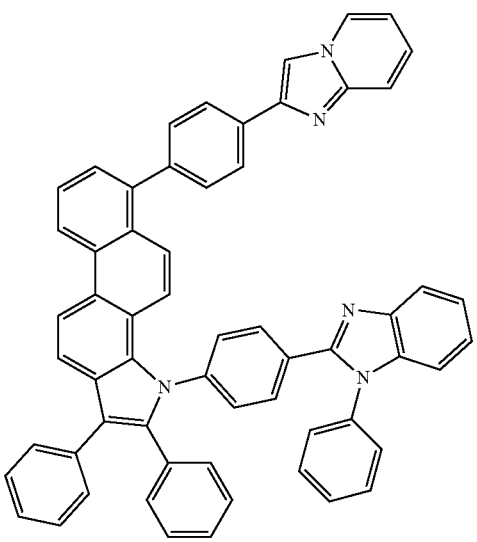
31
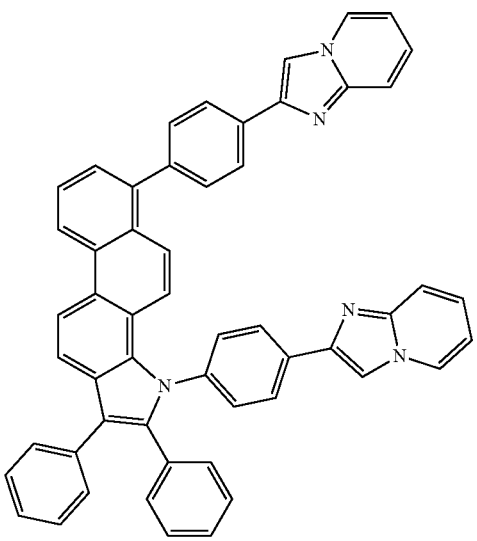

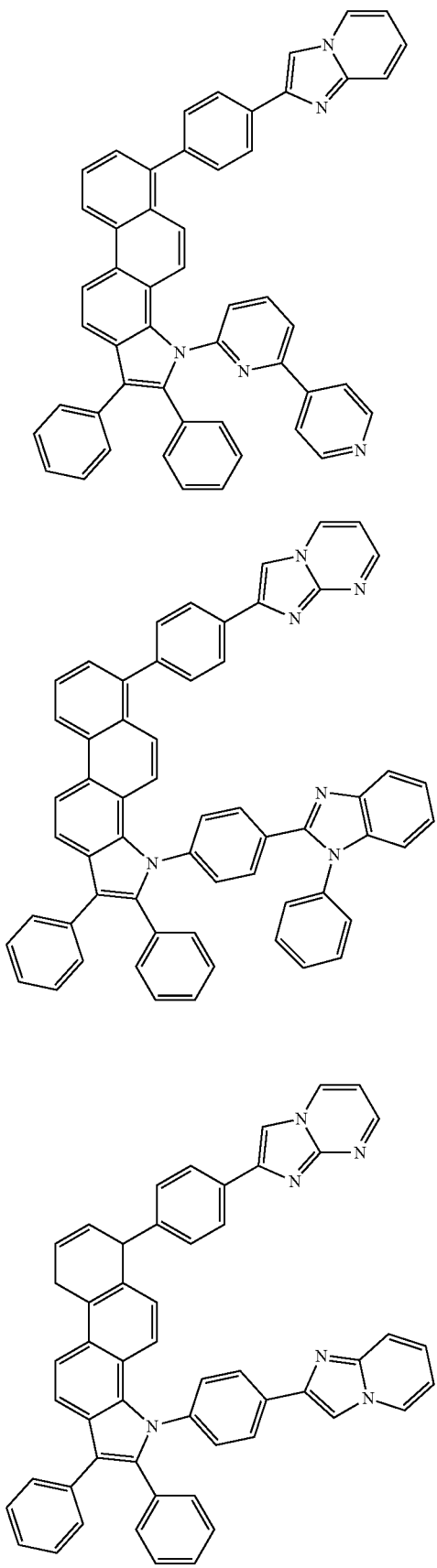
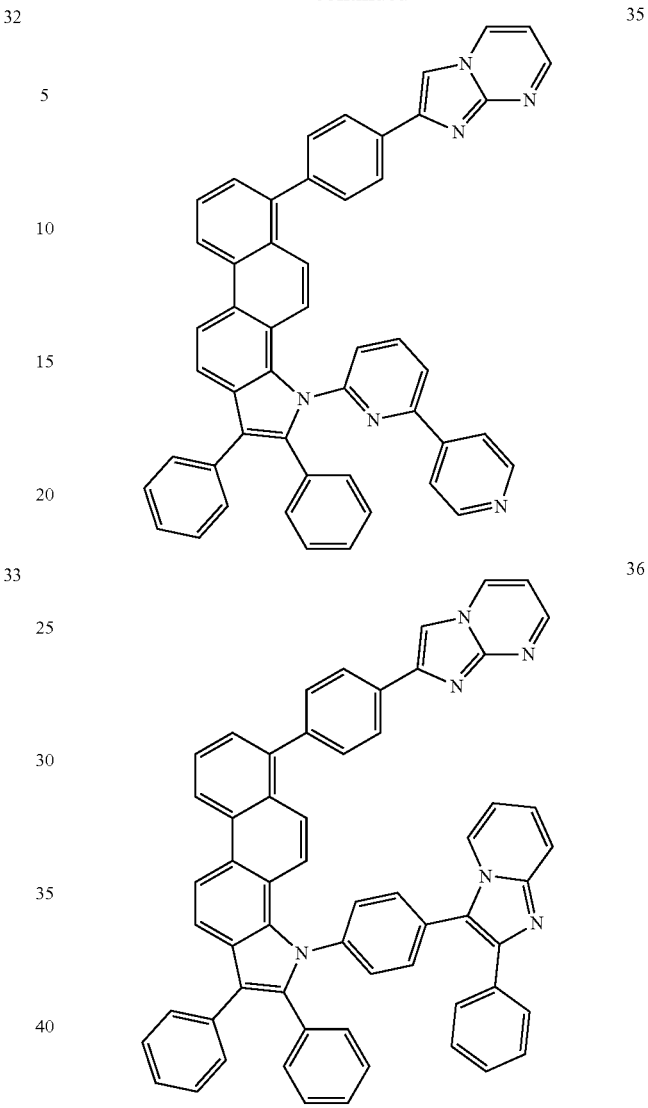

An organic light-emitting device according to embodiments of the present invention includes a first electrode, a second electrode, and an organic layer between the first electrode and the second electrode. The organic layer includes the heterocyclic compound of Formula 1 described above.

The organic layer including the heterocyclic compound of Formula 1 may be an electron injection layer, a hole transport layer, or a single layer having both electron injection and electron transport capabilities. Alternatively, the organic layer including the heterocyclic compound of Formula 1 may be an emission layer. When the organic layer including the heterocyclic compound of Formula 1 is an emission layer, the heterocyclic compound of Formula 1 may be a fluorescent host, a phosphorescent host, or a fluorescent dopant.

According to embodiments of the present invention, when the emission layer, the hole injection layer or the hole transport layer includes the heterocyclic compound of Formula 1, the emission layer may include an anthracene compound, an arylamine compound or a styryl compound, where the anthracene compound, the arylamine compound or the styryl compound may be unsubstituted or substituted with a substituent such as those described with reference to the unsubstituted $C_1$-$C_{50}$ alkyl group.

In some embodiments of the present invention, when the hole injection layer or the hole transport layer includes the heterocyclic compound of Formula 1, a red emission layer, a green emission layer, a blue emission layer, or a white emission layer may include a fluorescent compound.

The first electrode may be an anode, and the second electrode may be a cathode, but the reverse is also possible.

The organic layer may further include at least one layer selected from a hole injection layer, a hole transport layer, an electron blocking layer, an emission layer, a hole blocking layer, an electron transport layer and an electron injection layer, if desired.

For example, an organic light-emitting device according to embodiments of the present invention may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

According to embodiments of the present invention, the organic light emitting device may be a top-emission type organic light-emitting device or a bottom-emission type organic light-emitting device.

A method of manufacturing an organic light-emitting device according to embodiments of the present invention will now be described with reference to FIG. 1. FIG. 1 illustrates the structure of an organic light-emitting device according to an embodiment of the present invention. Referring to FIG. 1, an organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

First, the first electrode is formed on a substrate using a deposition or sputtering method. The first electrode may be formed of a first electrode material having a high work function. The first electrode may be an anode or a cathode. The substrate may be a substrate conventionally used in organic light-emitting devices, and may include, for example, a glass substrate or a transparent plastic substrate, which has excellent mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

Next, the HIL may be formed on the first electrode using various methods, for example, vacuum deposition, spin coating, casting, Langmuir-Blodgett (LB) deposition, or the like. When the HIL is formed using vacuum deposition, deposition conditions may vary according to the compound used to form the HIL, and the structure and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the compound used to form the HIL, and the structure and thermal properties of the HIL to be formed. For example, the coating conditions may include a coating speed of about 2000 rpm to about 5000 rpm, and a thermal treatment temperature of about 80° C. to about 200° C., wherein the thermal treatment serves to remove the solvent after coating.

The HIL material may include the heterocyclic compound of Formula 1 described above. Alternatively, known HIL materials may also be used. Nonlimiting examples of such HIL materials include phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline/poly(4-styrenesulfonate) (PANI/PSS).

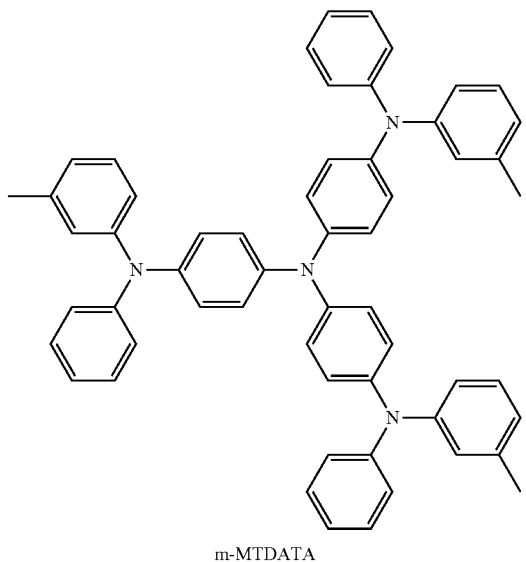

m-MTDATA

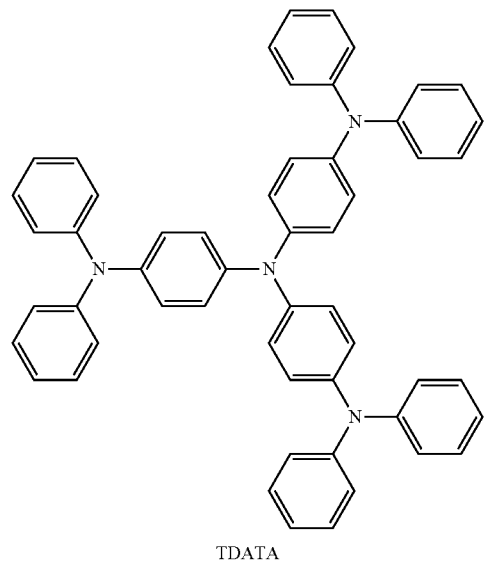

TDATA

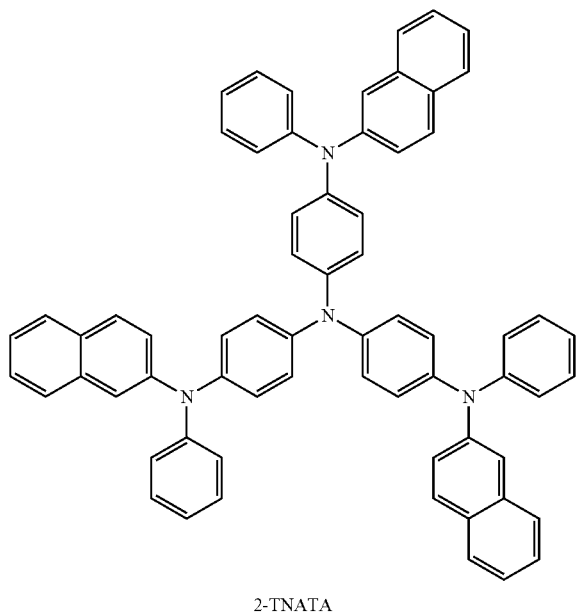

2-TNATA

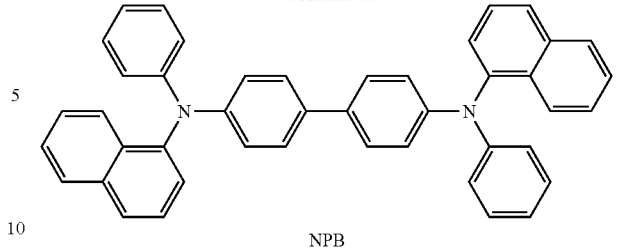

NPB

The HIL may have a thickness of about 100 Å to about 10,000 Å. For example, the HIL may have a thickness of about 100 Å to about 1000 Å. When the HIL has a thickness within these ranges, the HIL may have good hole injection characteristics without an increase in driving voltage.

Next, the HTL may be formed on the HIL using various methods, for example vacuum deposition, spin coating, casting, LB deposition, or the like. When the HTL is formed using vacuum deposition or spin coating, the deposition or coating conditions may be similar to those used to form the HIL, although the deposition or coating conditions may vary according to the material that is used to form the HTL.

The HTL material may include the heterocyclic compound of Formula 1 described above. Alternatively, known HTL materials may be used. Nonlimiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD). Among these materials, TCTA may not only transport holes but also inhibit excitons from being diffused from the EML.

The HTL may have a thickness of about 50 Å to about 1000 Å. For example, the HTL may have a thickness of about 100 Å to about 600 Å. When the HTL has a thickness within these ranges, the HTL may have good hole transport characteristics without a substantial increase in driving voltage.

Next, the EML may be formed on the HTL using various methods, for example, vacuum deposition, spin coating, casting, LB deposition, or the like. When the EML is formed using vacuum deposition or spin coating, the deposition or coating conditions may be similar to those used to form the HIL, although the deposition and coating conditions may vary according to the material that is used to form the EML.

The EML may include the heterocyclic compound of Formula 1 described above. In particular, the heterocyclic compound of Formula 1 may be used as a host or a dopant. The EML may be formed using a variety of known light-emitting materials, in addition to the heterocyclic compound of Formula 1. Alternatively, the EML may be formed using a known host and a dopant. The dopant used to form the EML may include either a fluorescent dopant or a phosphorescent dopant.

Nonlimiting examples of suitable hosts include Alq$_3$, CPB (4,4'-N,N'-dicarbazole-biphenyl), 9,10-di(naphthalen-2-yl) anthracene (ADN), and distyrylarylene (DSA).

Nonlimiting examples of red dopants include platinum(II) octaethylporphyrin (PtOEP), Ir(piq)$_3$, Btp$_2$Ir(acac), and DCJTB.

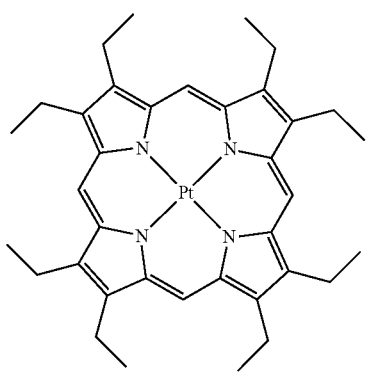

PtOEP

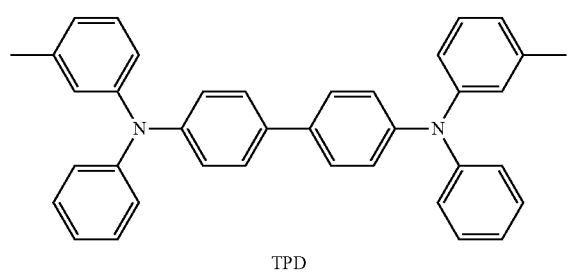

TPD

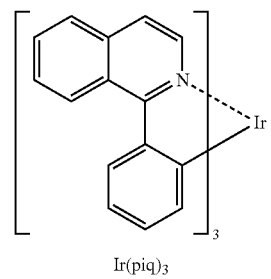

Ir(piq)$_3$

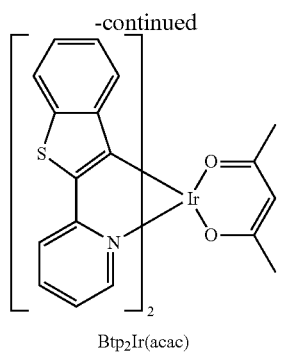

Btp₂Ir(acac)

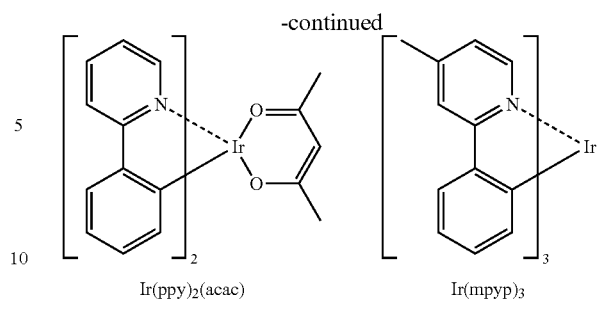

Ir(ppy)₂(acac)　　　　Ir(mpyp)₃

Nonlimiting examples of green dopants include Ir(ppy)₃ (where "ppy" denotes phenylpyridine), Ir(ppy)₂(acac), Ir(mpyp)₃, and C545T.

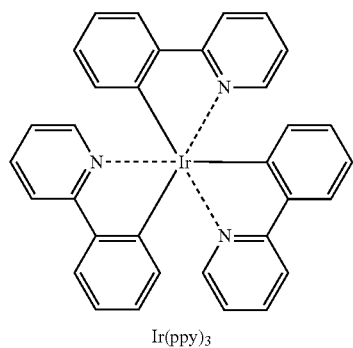

Ir(ppy)₃

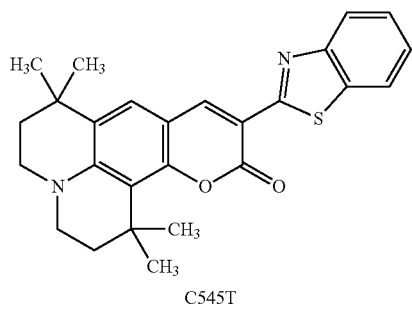

C545T

Nonlimiting examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP).

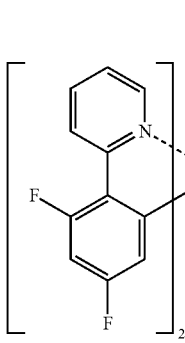

F₂Irpic

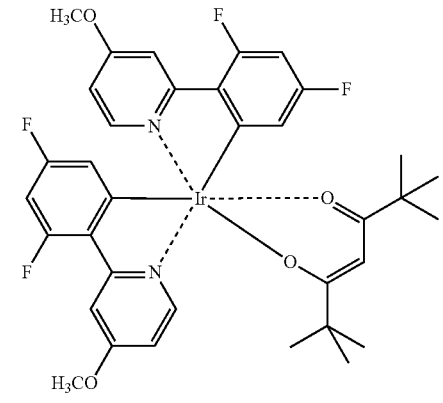

(F₂ppy)₂Ir(tmd)

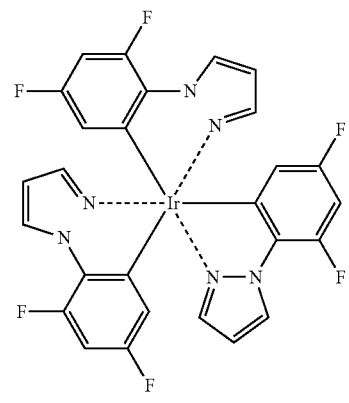

Ir(dfppz)₃

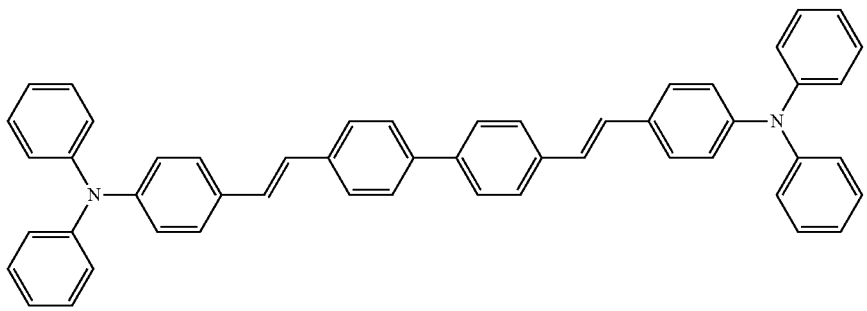

DPAVBi

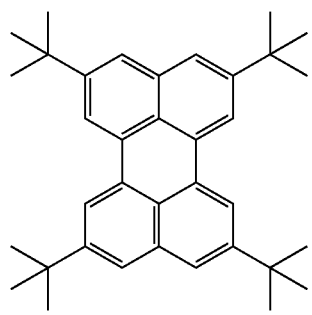

TBP

The amount of the dopant may be about 0.1 to about 20 parts by weight, or about 0.5 to about 12 parts by weight, based on 100 parts by weight of the EML material (which is equivalent to the total weight of the host and the dopant). When the amount of the dopant is within these ranges, concentration quenching may be substantially prevented.

The EML may have a thickness of about 100 Å to about 1000 Å. For example, the EML may have a thickness of about 200 Å to about 600 Å. When the EML has a thickness within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL, without limitation. Nonlimiting examples of such HBL materials include oxadiazole derivatives, triazole derivatives, phenathroline derivatives, Balq, and BCP.

The HBL may have a thickness of about 50 Å to about 1000 Å. For example, the HBL may have a thickness of about 100 Å to about 300 Å. When the HBL has a thickness within these ranges, the HBL may have excellent hole blocking characteristics without a substantial increase in driving voltage.

Next, the ETL is formed on the EML (or HBL) using various methods, for example, vacuum deposition, spin coating, casting, or the like. When the ETL is formed using vacuum deposition or spin coating, the deposition or coating conditions may be similar to those used to form the HIL, although the deposition and coating conditions may vary according to the material that is used to form the ETL.

The ETL material may include the heterocyclic compound of Formula 1 described above. Alternatively, the ETL may be formed of any known material. Nonlimiting examples of such ETL materials include quinoline derivatives, such as tris(8-quinolinolate)aluminum (Alq$_3$), TAZ, or Balq.

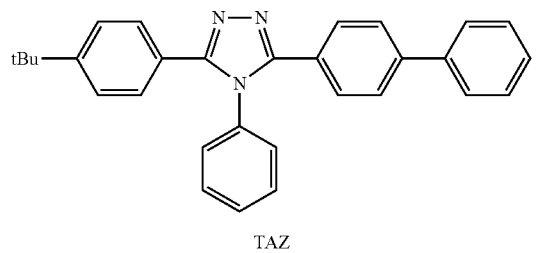

TAZ

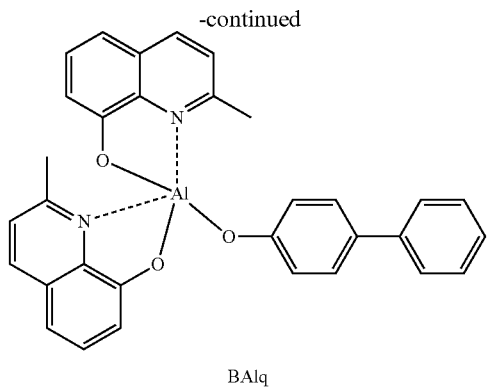

BAlq

The ETL may have a thickness of about 100 Å to about 1000 Å. For example, the ETL may have a thickness of about 100 Å to about 500 Å. When the ETL has a thickness within these ranges, the ETL may have good electron transport characteristics without a substantial increase in driving voltage.

In addition, the EIL, which facilitates injection of electrons from the cathode, may be formed on the ETL. An EIL material may include the heterocyclic compound of Formula 1 described above. Alternatively, known EIL materials, such as LiF, NaCl, CsF, Li$_2$O, or BaO, may be used to form the EIL. The deposition or coating conditions may be similar to those used to form the HIL, although the deposition and coating conditions may vary according to the material that is used to form the EIL.

The EIL may have a thickness of about 1 Å to 100 Å. For example, the EIL may have a thickness of about 5 Å to about 90 Å. When the EIL has a thickness within the above range, the EIL may have good electron injection characteristics without a substantial increase in driving voltage.

Finally, the second electrode may be formed on the EIL using, for example, vacuum deposition, sputtering, or the like. The second electrode may be a cathode or an anode. A second electrode material may include a metal, an alloy, an electrically conductive compound, or mixtures thereof, all of which have low work functions. Nonlimiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

According to embodiments of the present invention, at least one layer of the organic light-emitting device may be formed of the heterocyclic compound of Formula 1 and may be formed using a deposition method or a wet method of coating a solution of the heterocyclic compound of Formula 1.

The following Examples are presented for illustrative purposes only, and do not limit the scope of the present invention.

EXAMPLES

Synthesis Example 1

Synthesis of Intermediate 1

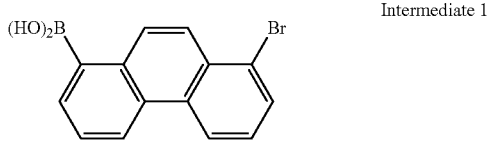 [SMILES: OB(O)c1cccc2c1ccc1c(Br)cccc12]

Intermediate 1

16.8 g (50 mmol) of 1,8-dibromophenanthrene was dissolved in 250 mL of THF in a nitrogen atmosphere, and the solution was cooled to −78° C. 20 mL (2.5 M in hexane) of N-butyl lithium was slowly added to the solution, and the mixture was stirred for 1 hour. Then, 11.5 mL (100 mmol) of B(OiPr)$_3$ was added thereto, and the mixture was heated to room temperature and stirred for 3 hours. After the reaction was completed, a 10% HCl aqueous solution was added thereto. The mixture was subjected to extraction three times with 500 mL of ethyl acetate. An organic layer was collected and dried using magnesium sulfate to evaporate the solvent. The residue was recrystallized with dichloromethane and normal hexane to obtain 15.3 g (yield: 65%) of Intermediate 1. This compound was identified using HR-MS. C$_{14}$H$_{10}$BBrO$_2$ Calculated value: 299.9957; Measured value: 299.9960

Synthesis Example 2

Synthesis of Intermediate 2

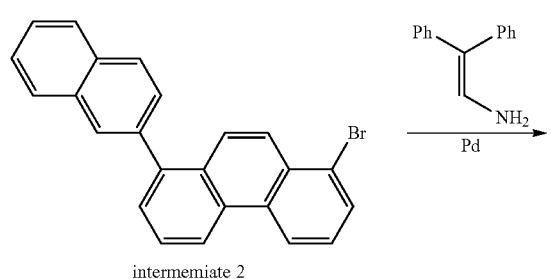

intermemiate 2

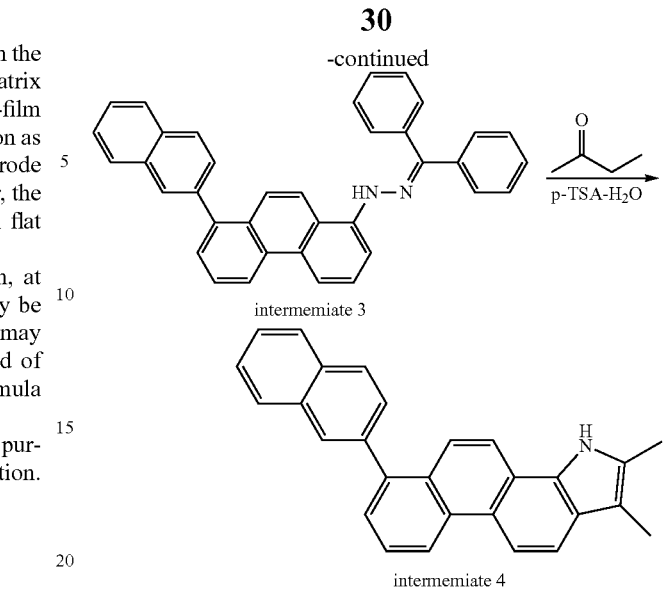

intermemiate 3 intermemiate 4

10.3 g (52 mmol) of 2-bromonaphthalene, 15.3 g (40 mmol) of Intermediate 1, 2.31 g (2.0 mmol) of Pd(PPh$_3$)$_4$ and 16.6 g (120 mmol) K$_2$CO$_3$ were dissolved in 200 mL of a mixed solution of THF/H$_2$O (2:1), and the mixture was stirred at 80° C. for 5 hours. The mixture was extracted with 600 ml of diethyl ether three times. An organic layer was collected and dried using magnesium sulfate to evaporate the solvent. The residue was recrystallized with dichloromethane and normal hexane to obtain 11.0 g (yield: 72%) of Intermediate 2. This compound was identified using HR-MS. C$_{24}$H$_{15}$Br Calculated value: 382.0357; Measured value: 382.0360

Synthesis Example 3

Synthesis of Intermediate 3

13.5 g (30 mmol) of Intermediate 2, 7.07 g (36 mmol) of benzophenone hydrazone, 4.32 g (45 mmol) of t-BuONa, 0.16 g (0.72 mmol) of and 0.30 g (0.72 mmol) of 2-dicyclohexylphosphino-2',4',6'-triisopropylbiphenyl were dissolved in 60 mL of toluene, and the mixture was stirred at 90° C. for 3 hours. The mixture was cooled to room temperature, and distilled water was added thereto. The mixture was subjected to extraction twice with 200 mL of diethylether and once with 200 mL of dichloromethane. An organic layer was collected and dried using magnesium sulfate, followed by filtration. Solvent was evaporated, and the residue was separated and purified using silica gel column chromatography to obtain 13.8 g (yield: 92%) of Intermediate 3. This compound was identified using HR-MS. C$_{37}$H$_{26}$N$_2$ Calculated value: 498.2096; Measured value: 498.2099

Synthesis Example 4

Synthesis of Intermediate 4

13.8 g (27.7 mmol) of Intermediate 3 and 10.5 g (55.4 mmol) of p-toluenesulfonic acid monohydrate were dissolved in 60 mL of methylethyl ketone, and the mixture was stirred at 110° C. for 24 hours. The mixture was cooled to room temperature, and distilled water was added thereto. The mixture was subjected to extraction twice with 100 mL of diethylether and twice with 100 mL of dichloromethane. An organic layer was collected and dried using magnesium sulfate, followed by filtration. Solvent was evaporated, and the residue was separated and purified using silica gel column chromatography to obtain 7.7 g (yield: 75%) of Intermediate 4. This compound was identified using HR-MS. $C_{28}H_{21}N$ Calculated value: 371.1674; Measured value: 371.1677

Synthesis Example 5

Synthesis of Intermediate 5

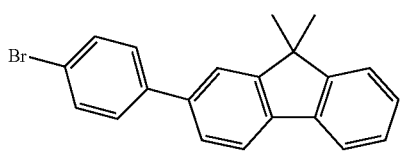

Intermediate 5

4.76 g (20 mmol) of 9,9'-dimethylfluorenyl-2-boronic acid, 6.22 g (22 mmol) of 1-bromo-4-iodobenzene, 1.16 g (1.0 mmol) of $Pd(PPh_3)_4$ and 11.0 g (80 mmol) of $K_2CO_3$ were dissolved in 100 mL of a mixed solution of $THF/H_2O$ (2:1), and the mixture was stirred at 80° C. for 5 hours. The mixture was subjected to extraction three times with 300 mL of diethyl ether. An organic layer was collected and dried using magnesium sulfate to evaporate the solvent. The residue was recrystallized with dichloromethane and normal hexane to obtain 5.1 g (yield: 73%) of Intermediate 5. This compound was identified using HR-MS. $C_{21}H_{17}Br$ Calculated value: 348.0514; Measured value: 348.0517

Synthesis Example 6

Synthesis of Compound 3

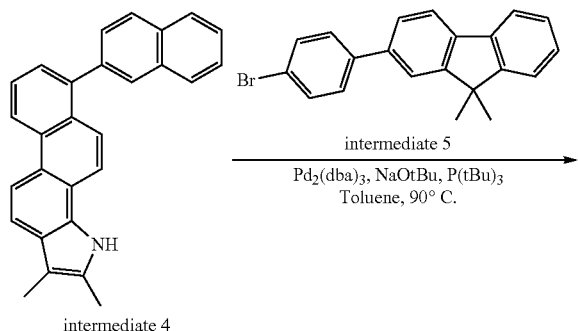

3.71 g (10 mmol) of Intermediate 4, 4.19 g (12 mmol) of Intermediate 5, 2.9 g (30 mmol) of t-BuONa, 366 mg (0.4 mmol) of $Pd_2(dba)_3$ and 80 mg (0.4 mmol) of $P(t-Bu)_3$ were dissolved in 60 mL of toluene in a nitrogen atmosphere, and the mixture was stirred at 90° C. for 3 hours. After the reaction was completed, the mixture was cooled to room temperature and subjected to extraction three times with distilled water and 50 ml of diethylether. An organic layer was collected and dried using magnesium sulfate to evaporate the solvent. The residue was separated and purified using silica gel column chromatography to obtain 4.6 g (yield: 72%) of Compound 3. $C_{49}H_{37}N$ Calculated value: 639.2926; Measured value: 639.2929; $^1H$ NMR ($CDCl_3$, 400 MHz) δ (ppm) 9.00 (d, 1H), 8.74 (d, 1H), 8.37 (dd, 2H), 7.99 (d, 1H), 7.91 (m, 4H), 7.77 (m, 2H), 7.63-7.48 (m, 5H), 7.24-7.18 (m, 3H), 7.03-6.86 (m, 4H), 6.23 (m, 2H), 2.29 (s, 3H), 2.22 (s, 3H), 1.85 (s, 6H).

Synthesis Example 7

Synthesis of Intermediate 6

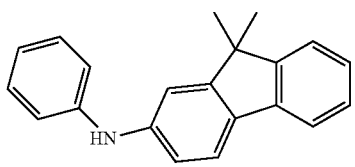

Intermediate 6

1.21 g (13 mmol) of phenylamine, 2.73 g (10 mmol) of 9,9'-dimethyl-2-bromofluorene, 1.44 g (15 mmol) of t-BuONa, 183 mg (0.2 mmol) of $Pd_2(dba)_3$, and 40 mg (0.2 mmol) of $P(t-Bu)_3$ were dissolved in 80 mL of toluene in a nitrogen atmosphere, and the mixture was stirred at 90° C. for 3 hours. After the reaction was completed, the mixture was cooled to room temperature and subjected to extraction three times with distilled water and 60 ml of diethylether. An organic layer was collected and dried using magnesium sulfate to evaporate the solvent. The residue was separated and purified using silica gel column chromatography to obtain 2.23 g (yield: 78%) of Intermediate 6. This compound was identified using HR-MS. $C_{21}H_{19}N$ Calculated value: 285.1517; Measured value: 285.1520

Synthesis Example 8

Synthesis of Intermediate 7

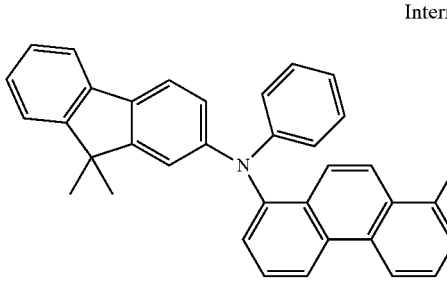

Intermediate 7

2.23 g (7.8 mmol) of Intermediate 6, 5.24 g (16 mmol) of 1,8-dibromophenanthrene, 1.12 g (12 mmol) of t-BuONa, 142 mg (0.16 mmol) of Pd$_2$(dba)$_3$, and 32 mg (0.16 mmol) of P(t-Bu)$_3$ were dissolved in 50 ml of toluene in a nitrogen atmosphere, and the mixture was stirred at 90° C. for 3 hours. After the reaction was completed, the mixture was cooled to room temperature and subjected to extraction three times with distilled water and 50 ml of diethylether. An organic layer was collected and dried using magnesium sulfate to evaporate the solvent. The residue was separated and purified using silica gel column chromatography to obtain 1.90 g (yield: 45%) of Intermediate 7. This compound was identified using HR-MS. C$_{35}$H$_{26}$BrN Calculate value: 539.1249; Measured value: 539.1253

Synthesis Example 9

Synthesis of Intermediate 8

Intermediate 8

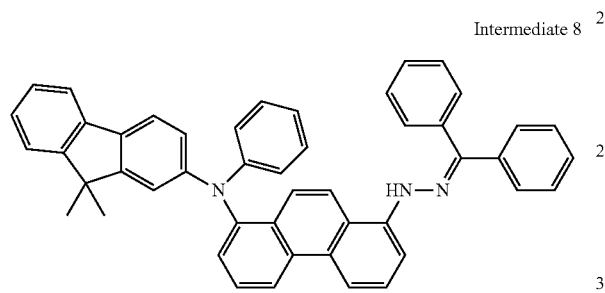

1.90 g (3.5 mmol) of Intermediate 7, 0.82 g (4.2 mmol) of benzophenone hydrazone, 0.50 g (5.3 mmol) of t-BuONa, 24 mg (0.11 mmol) of Pd(OAc)$_2$, and 45 mg (0.11 mmol) of 2-dicyclohexylphosphino-2',4',6'-triisopropylbiphenyl were dissolved in 20 mL of toluene, and the mixture was stirred at 90° C. for 3 hours. The mixture was cooled to room temperature, and distilled water was added thereto. The mixture was subjected to extraction twice with 50 mL of diethylether and once with 50 mL of dichloromethane. An organic layer was collected and dried using magnesium sulfate, followed by filtration. Solvent was evaporated, and the residue was separated and purified using silica gel column chromatography to obtain 2.0 g (yield: 87%) of Intermediate 8. This compound was identified using HR-MS. C$_{48}$H$_{37}$N$_3$ Calculated value: 655.2987; Measured value: 655.2990

Synthesis Example 10

Synthesis of Intermediate 9

Intermediate 9

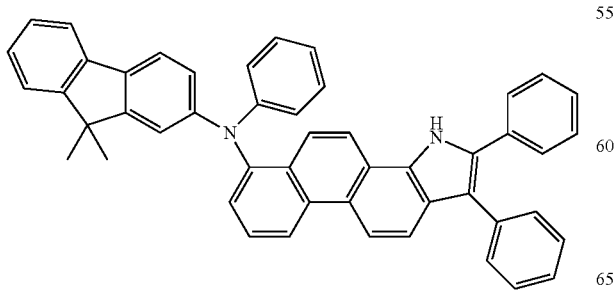

2.0 g (3.0 mmol) of Intermediate 8, 1.14 g (6.0 mmol) of p-toluenesulfonic acid monohydrate, 1.2 g (6.0 mmol) of benzylphenyl ketone were dissolved in 16 mL of ethanol and 4 mL of toluene, and the mixture was stirred at 110° C. for 24 hours. The mixture was cooled to room temperature, and distilled water was added thereto. The mixture was subjected to extraction twice with 25 mL of diethylether and twice with 25 mL of dichloromethane. An organic layer was collected and dried using magnesium sulfate, followed by filtration. Solvent was evaporated, and the residue was separated and purified using silica gel column chromatography to obtain 1.4 g (yield: 71%) of Intermediate 9. This compound was identified using HR-MS. C$_{49}$H$_{36}$N$_2$ Calculated: 652.2878; Measured: 652.2881

Synthesis Example 11

Synthesis of Compound 13

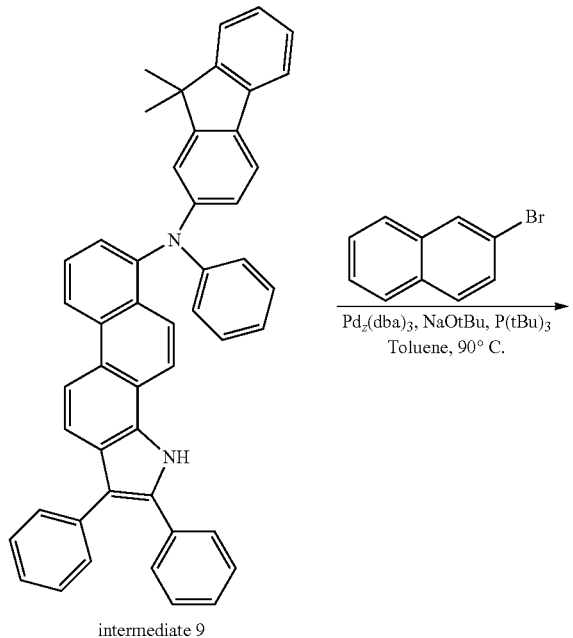

intermediate 9

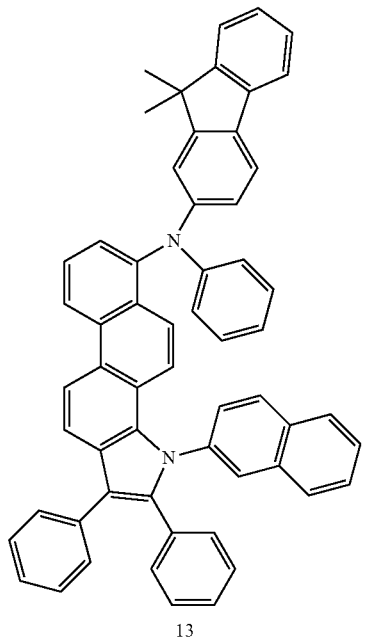

13

Compound 13 was synthesized with a yield of 72% in the same manner as Intermediate 3, except that Intermediate 9 was used instead of Intermediate 4, and 2-bromonaphthalene was used instead of Intermediate 5. This compound was identified using HR-MS. $C_{59}H_{42}N_2$ Calculated value: 778.3348; Measured value: 778.3351; $^1$H NMR (CDCl$_3$, 400 MHz) δ (ppm) 8.95 (d, 1H), 8.64 (d, 1H), 8.30 (dd, 2H), 8.05 (d, 1H), 7.98 (d, 1H), 7.81 (d, 1H), 7.73 (m, 1H), 7.70-7.45 (m, 10H), 7.43-7.20 (m, 11H), 7.12 (d, 1H), 6.94 (t, 1H), 6.62 (t, 1H), 6.31 (d, 1H), 6.08 (d, 1H), 5.66 (d, 2H), 1.85 (s, 6H).

Synthesis Example 12

Synthesis of Intermediate 10

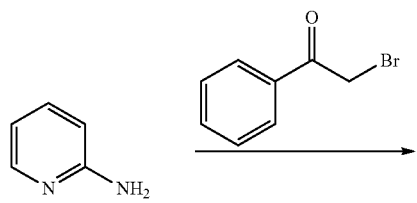

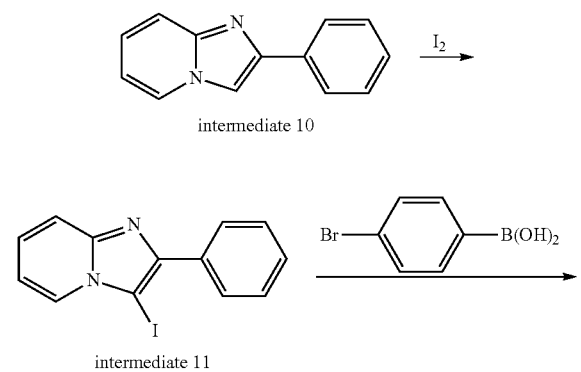

intermediate 11

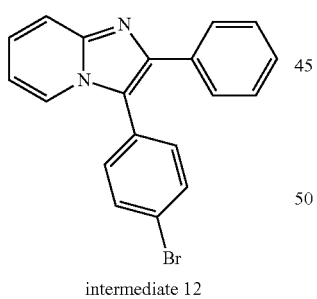

intermediate 12

1.99 g (10 mmol) of bromoacetophenone was dissolved in 50 mL of dimethoxyethane, and 1.0 g (10 mmol) of 2-aminopyridine was added thereto. The mixture was stirred at room temperature for 5 hours and stirred at 120° C. for 12 hours. After the reaction was completed, the mixture was cooled to room temperature, the solvent was removed, and 60 mL of dichloro methane was added thereto. A 10% sodium bicarbonate solution was added thereto to adjust the pH to 10, and the mixture was subjected to extraction using 50 mL of dichloro methane. An organic layer was collected and dried using magnesium sulfate to evaporate the solvent. The residue was separated and purified using silica gel column chromatography to obtain 1.2 g (yield: 65%) of Intermediate 10. This compound was identified using HR-MS. $C_{13}H_{10}N_2$ Calculate value: 194.0844; Measured value: 194.0847

Synthesis Example 13

Synthesis of Intermediate 11

400 g (2 mmol) of Intermediate 10 was dissolved in 10 mL of pyridine, and 760 g (3 mmol) of iodine was added thereto. The mixture was stirred at 50° C. for 5 hours, and an oxalic acid solution was added thereto to terminate the reaction. The mixture was subjected to extraction using 10 mL of dichloro methane, and then an organic layer was collected and dried using magnesium sulfate to evaporate the solvent. The residue was separated and purified using silica gel column chromatography to obtain 462 mg (yield: 72%) of Intermediate 11. This compound was identified using HR-MS. $C_{13}H_9IN_2$ Calculated value: 319.9810; Measured value: 319.9813

Synthesis Example 14

Synthesis of Intermediate 12

2.01 g (10 mmol) of 4-bromophenyl boronic acid, 4.16 g (13 mmol) of Intermediate 11, 0.58 g (0.5 mmol) of Pd(PPh$_3$)$_4$, and 5.53 g (40 mmol) of K$_2$CO$_3$ were dissolved in 50 ml of a mixed solution of THF/H$_2$O (2:1), and the mixture was stirred at 80° C. for 5 hours. The mixture was subjected to extraction three times with 100 mL of diethyl ether. An organic layer was collected and dried using magnesium sulfate to evaporate the solvent. The residue was recrystallized with dichloromethane and normal hexane to obtain 2.8 g (yield: 79%) of Intermediate 12. This compound was identified using HR-MS. $C_{19}H_{13}BrN_2$ Calculated value: 348.0262; Measured value: 348.0265

Synthesis Example 15

Synthesis of Intermediate 13

Intermediate 13

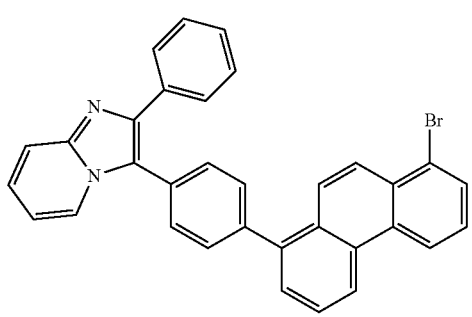

Intermediate 13 was synthesized with a yield of 75% in the same manner as that of Intermediate 2, except that Intermediate 12 was used instead of 2-bromonaphthalene. This compound was identified using HR-MS. $C_{33}H_{21}BrN_2$ Calculated value: 524.0888; Measured value: 524.0891

Synthesis Example 16

Synthesis of Intermediate 14

Intermediate 14

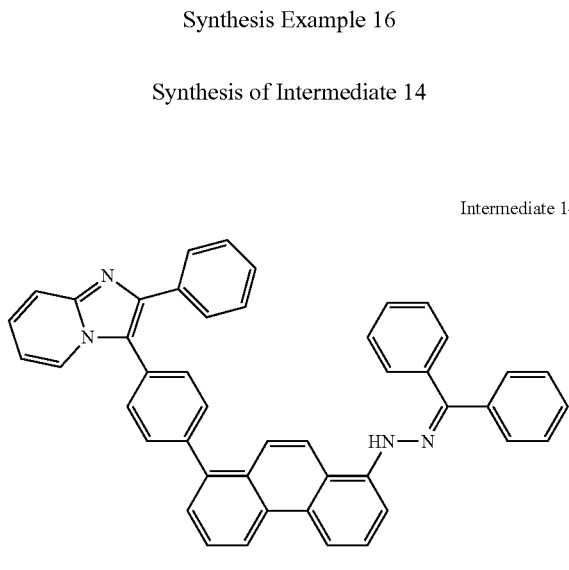

Intermediate 14 was synthesized with a yield of 69% in the same manner as Intermediate 8, except that Intermediate 13 was used instead of Intermediate 7. This compound was identified using HR-MS. $C_{46}H_{32}N_4$ Calculated value: 640.2627; Measured value: 640.2630

Synthesis Example 17

Synthesis of Intermediate 15

Intermediate 15

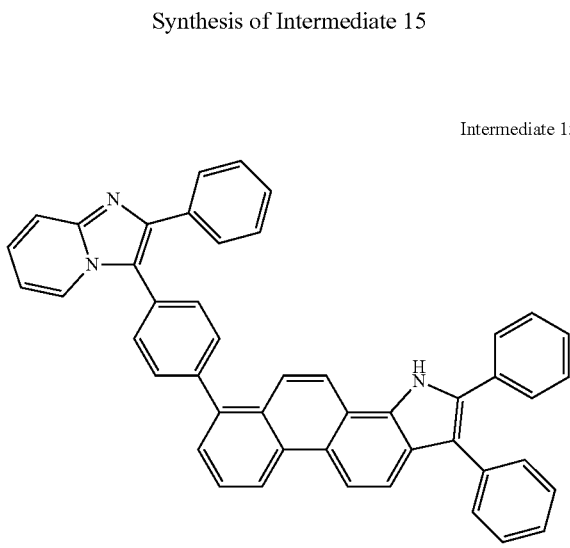

Intermediate 15 was synthesized with a yield of 68% in the same manner as Intermediate 9, except that Intermediate 14 was used instead of Intermediate 8. This compound was identified using HR-MS. $C_{47}H_{31}N_3$ Calculated value: 637.2518; Measured value: 637.2521

Synthesis Example 18

Synthesis of Compound 19

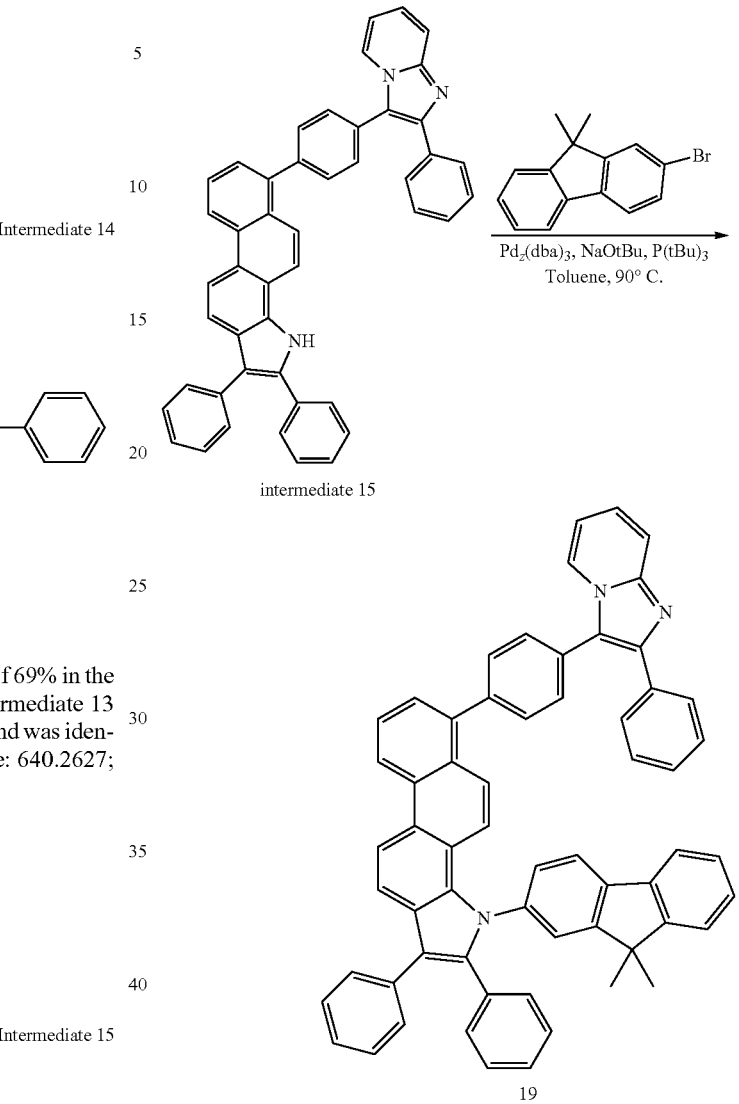

intermediate 15

19

Compound 19 was synthesized with a yield of 76% in the same manner as Compound 3, except that Intermediate 15 was used instead of Intermediate 4, and 9,9'-dimethyl-2-bromofluorene was used instead of Intermediate 5. This compound was identified using HR-MS. $C_{62}H_{43}N_3$ Calculated value: 829.3457; Measured value: 829.3460; $^1$H NMR (CDCl$_3$, 400 MHz) δ (ppm) 9.23 (d, 1H), 8.75 (d, 1H), 8.31 (d, 1H), 8.10 (dd, 2H), 7.88 (d, 1H), 7.81 (d, 2H), 7.64-7.45 (m, 11H), 7.39-7.22 (m, 13H), 7.09 (d, 1H), 6.95 (t, 1H), 6.84 (m, 2H), 6.47 (m, 1H), 1.85 (s, 6H).

Synthesis Example 19

Synthesis of Intermediate 16

Intermediate 16

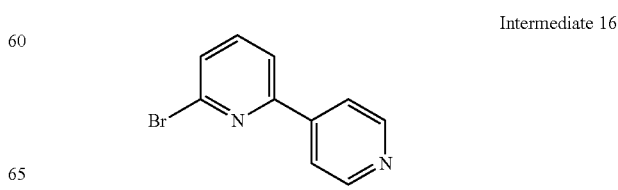

3.08 g (13 mmol) of 2,5-dibromo pyridine, 1.23 g (10 mmol) of 4-pyridyl boronic acid, 0.58 g (0.5 mmol) of Pd(PPh$_3$)$_4$, and 5.53 g (40 mmol) of K$_2$CO$_3$ were dissolved in 50 ml of a mixed solution of THF/H$_2$O (2:1), and the mixture was stirred at 80° C. for 5 hours. The mixture was subjected to extraction three times with 60 mL of diethyl ether. An organic layer was collected and dried using magnesium sulfate to evaporate the solvent. The residue was recrystallized with dichloromethane and normal hexane to obtain 1.74 g (yield: 74%) of Intermediate 16. This compound was identified using HR-MS. C$_{10}$H$_7$BrN$_2$ Calculated value: 233.9793; Measured value: 233.9796

Synthesis Example 20

Synthesis of Intermediate 17

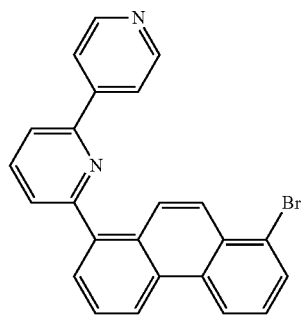

Intermediate 17

Intermediate 17 was synthesized with a yield of 76% in the same manner as Intermediate 2, except that Intermediate 16 was used instead of 2-bromonaphthalene. This compound was identified using HR-MS. C$_{24}$H$_{15}$BrN$_2$ Calculated value: 410.0419; Measured value: 410.0422

Synthesis Example 21

Synthesis of Intermediate 18

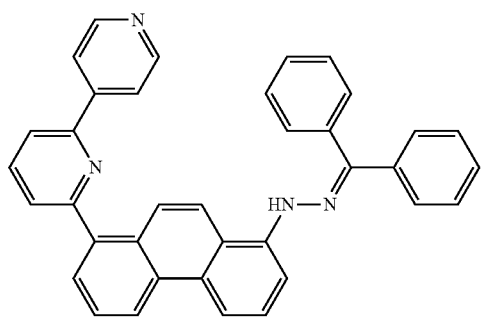

Intermediate 18

Intermediate 18 was synthesized with a yield of 70% in the same manner as Intermediate 8, except that Intermediate 17 was used instead of Intermediate 7. This compound was identified using HR-MS. C$_{37}$H$_{26}$N$_4$ Calculated value: 526.2157; Measured value: 526.2160

Synthesis Example 22

Synthesis of Intermediate 19

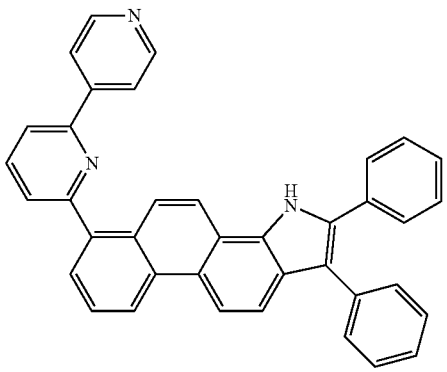

Intermediate 19

Intermediate 19 was synthesized with a yield of 62% in the same manner as Intermediate 9, except that Intermediate 18 was used instead of Intermediate 8. This compound was identified using HR-MS. C$_{38}$H$_{25}$N$_3$ Calculated value: 523.2048; Measured value: 523.2051

Synthesis Example 18

Synthesis of Compound 29

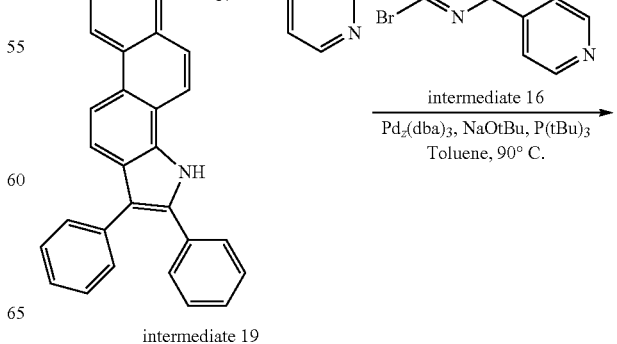

intermediate 19

-continued

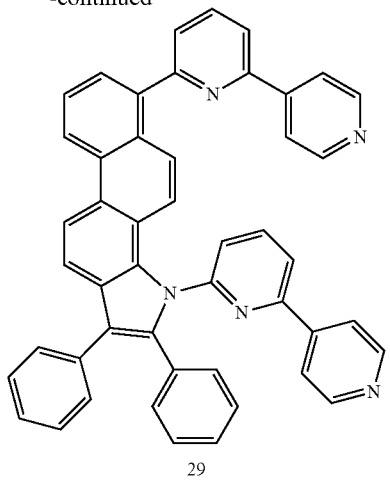
29

Compound 29 was synthesized with a yield of 70% in the same manner as Intermediate 3, except that Intermediate 19 was used instead of Intermediate 4, and Intermediate 16 was used instead of Intermediate 5. This compound was identified using HR-MS. $C_{48}H_{31}N_5$ Calculated value: 677.2579; Measured value: 677.2582; $^1$H NMR (CDCl$_3$, 400 MHz) δ (ppm) 9.23 (d, 1H), 8.75 (d, 1H), 8.61-8.56 (m, 4H), 8.38 (d, 1H), 8.27 (t, 1H), 8.09 (t, 2H), 7.90-7.81 (m, 4H), 7.73 (m, 2H), 7.62 (m, 2H), 7.54 (m, 2H), 7.50 (m, 2H), 7.41-7.25 (m, 9H).

Example 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the anode was mounted in a vacuum deposition apparatus.

2-TNATA was vacuum-deposited on the glass substrate to form a HIL having a thickness of 600 Å, and then 4,4'-bis[N-(1-naphthyl)-N-phenylamino]biphenyl (NPB) (as a hole transport compound) was vacuum deposited on the HIL to form a HTL having a thickness of 300 Å.

Then, Alq$_3$ (as a green fluorescent host) and C545T (as a green fluorescent dopant) were simultaneously deposited on the HTL in a weight ratio of 98:2 to form an EML having a thickness of 300 Å.

Then, Compound 3 was deposited on the EML to form an ETL having a thickness of 300 Å, and then LiF, which is a halogenated alkali metal, was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

The organic light-emitting device had a driving voltage of 6.15V at a current density of 50 mA/cm$^2$, a high brightness of 7,130 cd/m$^2$, color coordinates of (0.311, 0.642), and an emission efficiency of 14.26 cd/A.

Example 2

An organic light-emitting device was manufactured in the same manner as in Example 1, except that Compound 13 was used instead of Compound 3 to form the ETL.

The organic light-emitting device had a driving voltage of 6.98V at a current density of 50 mA/cm$^2$, a high brightness of 6,205 cd/m$^2$, color coordinates of (0.310, 0.642), and an emission efficiency of 12.41 cd/A.

Example 3

An organic light-emitting device was manufactured in the same manner as in Example 1, except that Compound 19 was used instead of Compound 3 to form the ETL.

The organic light-emitting device had a driving voltage of 5.68V at a current density of 50 mA/cm$^2$, a high brightness of 8,435 cd/m$^2$, color coordinates of (0.309, 0.643), and an emission efficiency of 16.87 cd/A.

Example 4

An organic light-emitting device was manufactured in the same manner as in Example 1, except that Compound 29 was used instead of Compound 3 to form the ETL.

The organic light-emitting device had a driving voltage of 5.92V at a current density of 50 mA/cm$^2$, a high brightness of 7,620 cd/m$^2$, color coordinates of (0.309, 0.642), and an emission efficiency of 15.24 cd/A.

Comparative Example 1

An organic light-emitting device was manufactured in the same manner as in Example 1, except that Alq$_3$ was used instead of Compound 3 to form the ETL.

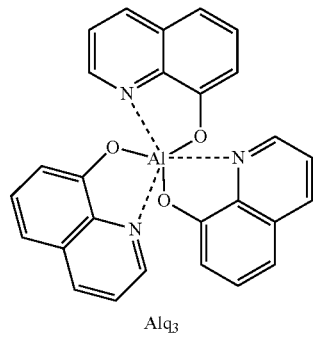
Alq$_3$

The organic light-emitting device had a driving voltage of 7.45V at a current density of 50 mA/cm$^2$, a brightness of 6,102 cd/m$^2$, color coordinates of (0.309, 0.642), and an emission efficiency of 12.2 cd/A.

The organic light-emitting devices manufactured using the heterocyclic compounds of Formula 1 according to embodiments of the present invention had driving voltages that were lower by 1V or greater than devices using Alq$_3$, and thus had high efficiency and good I-V-L characteristics. In particular, lifetime characteristics were improved by 100% or greater in the organic light-emitting devices according to Examples 1 through 4 compared with the organic light-emitting device according to Comparative Example 1. The results are shown in Table 1 below.

TABLE 1

|  | ETL material | Driving voltage | Current density | Brightness | Efficiency [%] | Color coordinates | Half-life span (hr @ 100 mA/cm$^2$) |
|---|---|---|---|---|---|---|---|
| Example 1 | Compound 3 | 6.15 | 50 | 7,130 | 14.26 | (0.311, 0.642) | 435 hr |
| Example 2 | Compound 13 | 6.98 | 50 | 6,205 | 12.41 | (0.310, 0.642) | 326 hr |
| Example 3 | Compound 19 | 5.68 | 50 | 8,435 | 16.87 | (0.309, 0.643) | 510 hr |
| Example 4 | Compound 29 | 5.92 | 50 | 7,620 | 15.24 | (0.309, 0.642) | 493 hr |
| Comparative Example 1 | Alq$_3$ | 7.45 | 50 | 6,102 | 12.2 | (0.309, 0.642) | 237 hr |

The heterocyclic compounds according to embodiments of the present invention have good electrical characteristics, charge transporting capabilities, emitting capabilities, high glass transition temperatures, and anti-crystallization characteristics, and thus may be used as electron injecting materials and/or emitting materials for all-color fluorescent and phosphorescent devices, such as red, green, blue, and white fluorescent and phosphorescent devices. Thus, an organic light-emitting device with high-efficiency, low driving voltage, high brightness and long lifespan may be manufactured using the heterocyclic compounds.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1 below:

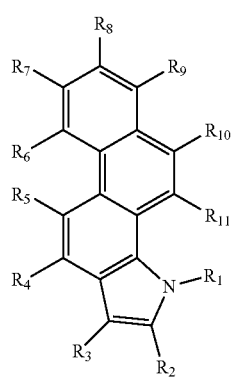

Formula 1 wherein each of $R_1$ through $R_{11}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $C_5$-$C_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, wherein;

$R_9$ is selected from the group consisting of:
  unsubstituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups;
  unsubstituted $C_4$-$C_{60}$ heteroaryl groups;
  unsubstituted $C_5$-$C_{50}$ arylamine groups;
  substituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups;
  substituted $C_4$-$C_{60}$ heteroaryl groups substituted with at least one substituent selected from the group consisting of $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups; and
  substituted $C_5$-$C_{50}$ arylamine groups substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups, wherein two or more adjacent substituents selected from $R_1$ through $R_{11}$ may optionally combine to form an aromatic ring.

2. The heterocyclic compound of claim 1, wherein $R_1$ is selected from the group consisting of
  unsubstituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups;
  unsubstituted $C_4$-$C_{60}$ heteroaryl groups;
  substituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups; and substituted $C_4$-$C_{60}$ heteroaryl groups substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups.

3. The heterocyclic compound of claim 1, wherein each of $R_2$ and $R_3$ is independently selected from the group consisting of methyl groups and phenyl groups.

4. The heterocyclic compound of claim 1, wherein the compound represented by Formula 1 is selected from the group consisting of Compounds 3, 13, 19 and 29:

3

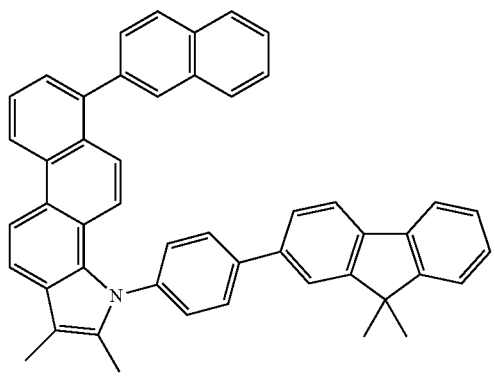

13

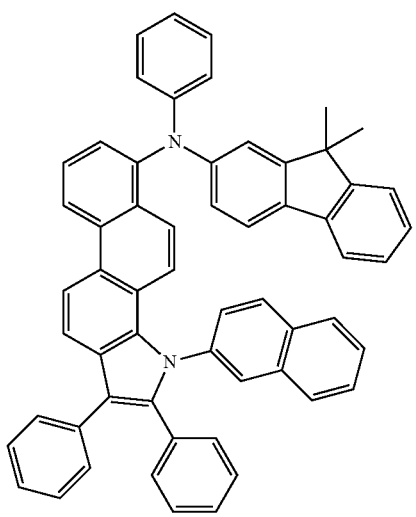

19

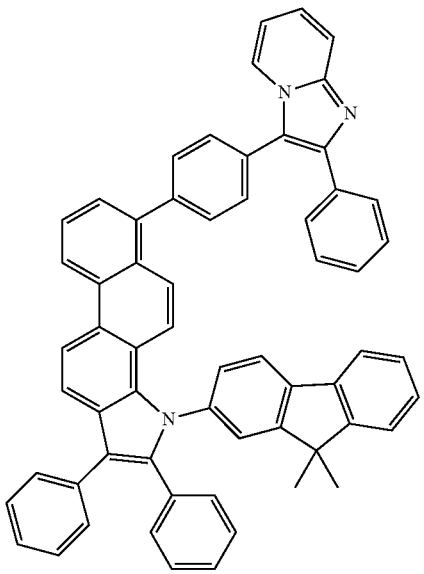

29

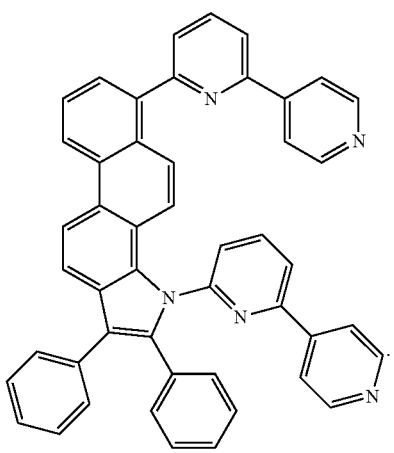

5. An organic light-emitting device comprising:
a first electrode;
a second electrode; and
an organic layer between the first electrode and the second electrode,
wherein the organic layer comprises the heterocyclic compound of claim 1.

6. The organic light-emitting device of claim 5, wherein the organic layer comprises an electron injection layer or an electron transport layer.

7. The organic light-emitting device of claim 5, wherein the organic layer comprises a single layer having both electron injection and electron transport capabilities.

8. The organic light-emitting device of claim 5, wherein the organic layer comprises an emission layer.

9. The organic light-emitting device of claim 5, wherein the organic layer comprises an emission layer, and the heterocyclic compound is a host for a fluorescent or phosphorescent device.

10. The organic light-emitting device of claim 5, wherein the organic layer comprises an emission layer, and the heterocyclic compound is a fluorescent dopant.

11. The organic light-emitting device of claim 5, wherein the organic layer comprises an emission layer, and an electron injection layer or an electron transport layer, wherein the emission layer comprises an anthracene compound or an arylamine compound or a styryl compound.

12. The organic light-emitting device of claim 5, wherein the organic layer comprises an emission layer, and an electron injection layer or an electron transport layer, wherein the emission layer comprises a red emission layer, a green emission layer, a blue emission layer or a white emission layer that comprises a phosphorescent compound.

13. The organic light-emitting device of claim 5, wherein the organic layer comprises at least one layer selected from the group consisting of a hole injection layer, a hole transport layer, an electron blocking layer, an emission layer, a hole blocking layer, an electron transport layer, and an electron injection layer.

14. The organic light-emitting device of claim 5, wherein the organic-light emitting device comprises a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

15. A flat panel display device comprising the organic light-emitting device of claim 5, wherein the first electrode of the organic light-emitting device is electrically connected to a source electrode or a drain electrode of a thin-film transistor.

16. An organic light-emitting device comprising:
a first electrode;
a second electrode; and
an organic layer between the first electrode and the second electrode,
wherein the organic layer comprises at least one layer comprising the heterocyclic compound of claim 1, the at least one layer being formed using a wet process.

17. An organic light-emitting device comprising:
a first electrode;
a second electrode; and
an organic layer between the first electrode and the second electrode,
wherein the organic layer comprises a heterocyclic compound comprising a compound represented by Formula 1:

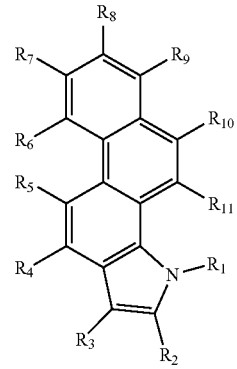

Formula 1 wherein each of $R_1$ through $R_{11}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $C_5$-$C_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, wherein two or more adjacent substituents selected from $R_1$ through $R_{11}$ may optionally combine to form an aromatic ring.

* * * * *